United States Patent
Yamaguchi et al.

[11] Patent Number: 5,133,856
[45] Date of Patent: Jul. 28, 1992

[54] ION SENSOR

[75] Inventors: Shuichiro Yamaguchi, Fuji; Norihiko Ushizawa; Takeshi Shimomura, both of Fujinomiya; Noboru Oyama, Higashikurume, all of Japan

[73] Assignee: Terumo Kabushiki Kaisha, Tokyo, Japan

[21] Appl. No.: 577,050

[22] Filed: Sep. 4, 1990

Related U.S. Application Data

[63] Continuation of Ser. No. 402,969, Sep. 6, 1989, abandoned, Ser. No. 168,634, Feb. 29, 1988, abandoned, Ser. No. 29,400, Mar. 23, 1987, abandoned, and Ser. No. 813,556, Dec. 26, 1985, abandoned.

[30] Foreign Application Priority Data

| Dec. 28, 1984 | [JP] | Japan | 59-281076 |
| Feb. 25, 1985 | [JP] | Japan | 60-35691 |
| Mar. 19, 1985 | [JP] | Japan | 60-53308 |
| Mar. 19, 1985 | [JP] | Japan | 60-55177 |
| Apr. 30, 1985 | [JP] | Japan | 60-93176 |

[51] Int. Cl.$^5$ .................................. G01N 27/26
[52] U.S. Cl. ............................ 204/416; 204/415; 204/418
[58] Field of Search .......... 204/290 R, 98, 402, 204/409, 290 F, 415, 418, 416

[56] References Cited

U.S. PATENT DOCUMENTS

| 3,598,713 | 8/1971 | Baum et al. |  |
| 3,932,233 | 1/1976 | Ruzicka et al. |  |
| 3,957,612 | 5/1976 | Niedrach | 204/418 |
| 4,115,209 | 9/1978 | Freiser et al. |  |
| 4,214,968 | 7/1980 | Battaglia et al. | 204/416 |
| 4,454,007 | 6/1984 | Pace | 204/416 |
| 4,510,034 | 4/1985 | Ohshima et al. | 204/290 F |
| 4,511,442 | 4/1985 | Pellegri | 204/98 |
| 4,541,905 | 9/1985 | Kuwana et al. | 204/290 R |
| 4,549,951 | 10/1985 | Knudson | 204/416 |
| 4,563,263 | 1/1986 | Oyama | 204/418 |
| 4,566,949 | 1/1986 | Berger | 204/402 |
| 4,576,706 | 3/1986 | Takata et al. | 204/409 |

OTHER PUBLICATIONS

Analytical Chemistry, 54 (7), 1982, pp. 1224–1227.
Analytical Chemistry, 56 (3), 1984, pp. 535–538.
J. Of Analytical Chemistry, 34 (8), Part 1, 1979, pp. 1159–1162.

*Primary Examiner*—John Niebling
*Assistant Examiner*—Bruce F. Bell
*Attorney, Agent, or Firm*—Cushman, Darby & Cushman

[57] ABSTRACT

An ion sensor of the type wherein a specific type of ion in an aqueous solution is measured by potential response. The sensor includes a conductor base, and a reversible redox polymer film formed directly on a surface of said conductor base. An ion carrier film is formed directly on a surface of said redox polymer film. The carrier film contains an ion carrier substance for allowing the specific type of ions to permeate from the aqueous solution to said polymer film.

33 Claims, 26 Drawing Sheets

F I G. 2
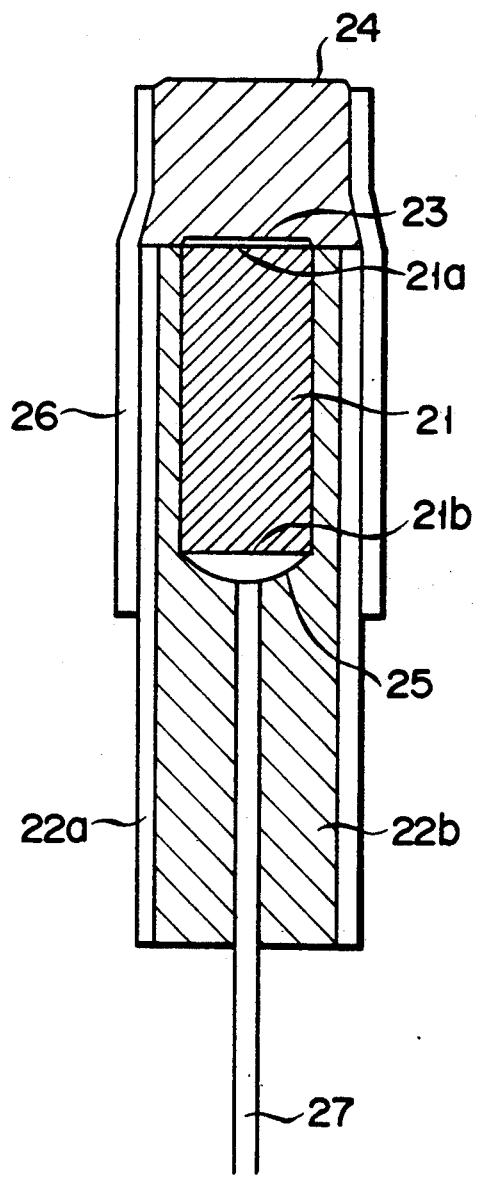

F I G. 21
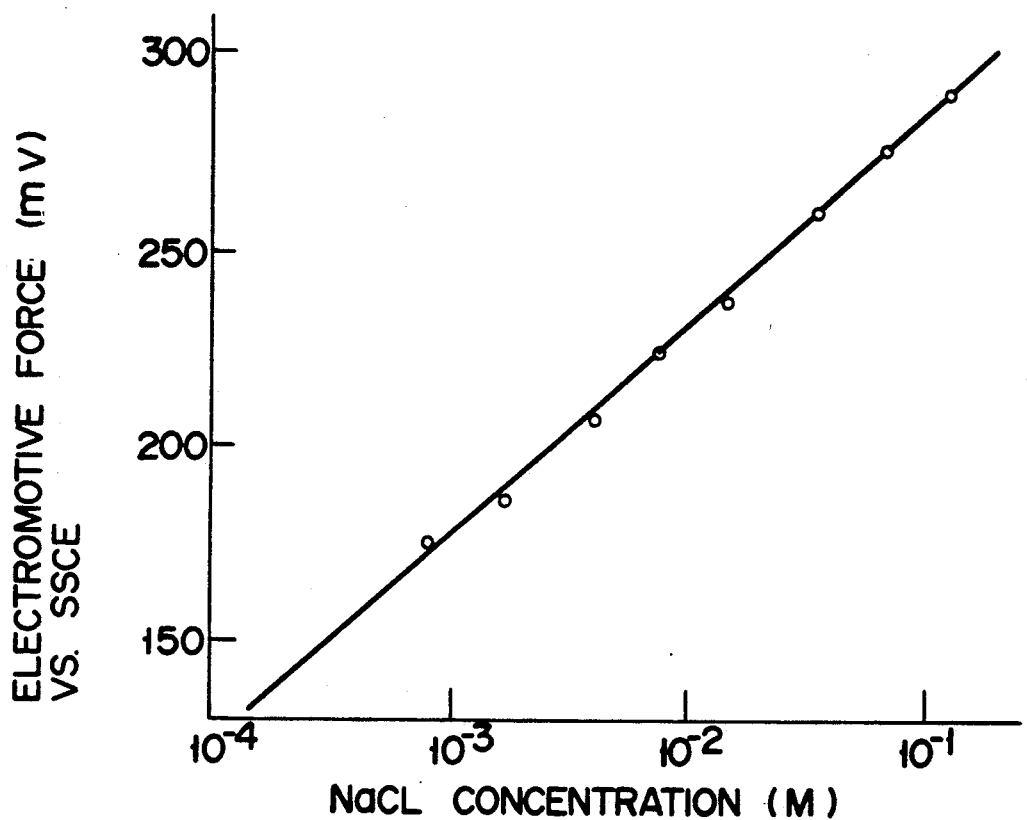
F I G. 22
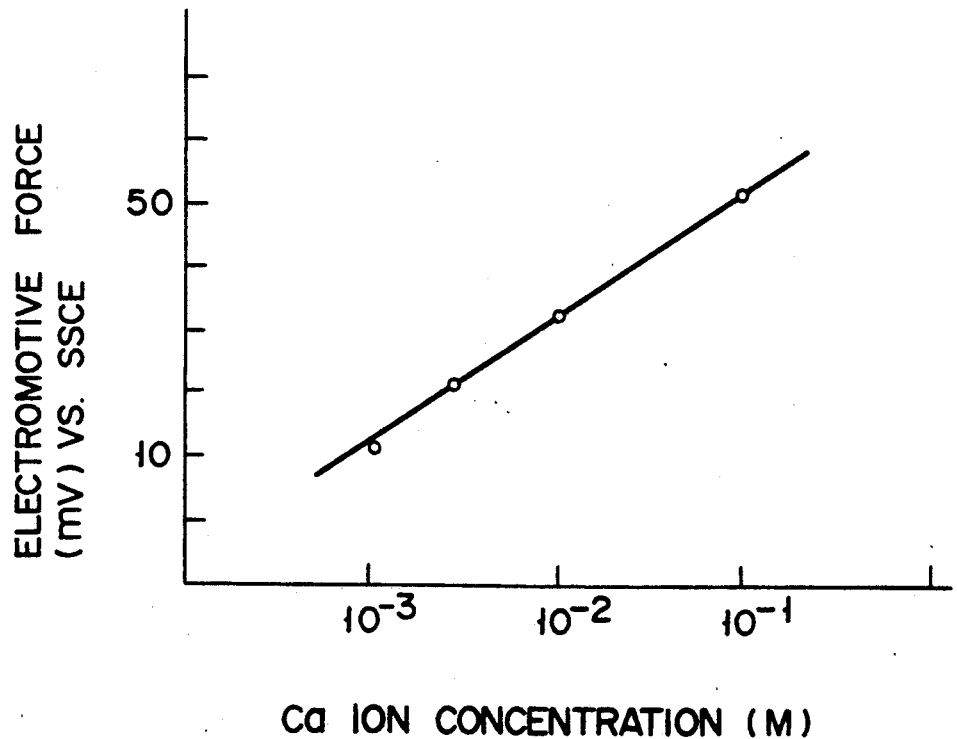

F I G. 26
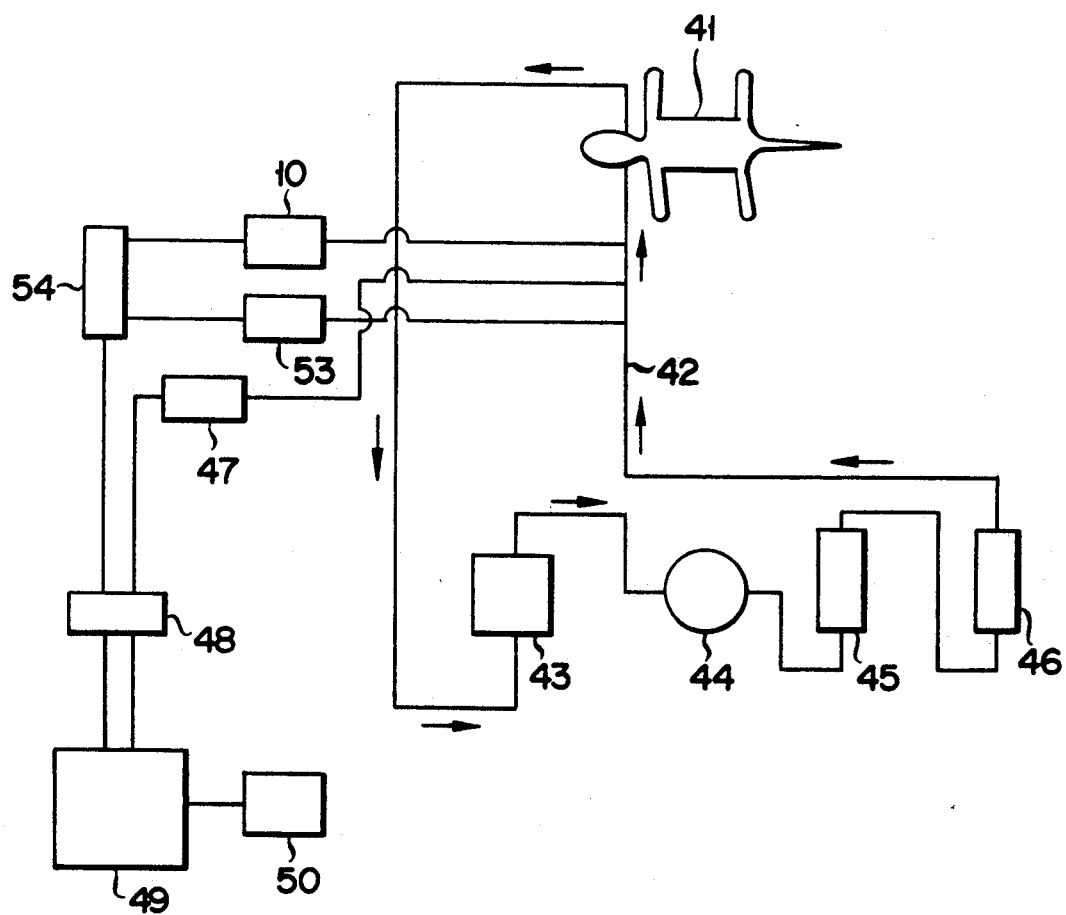

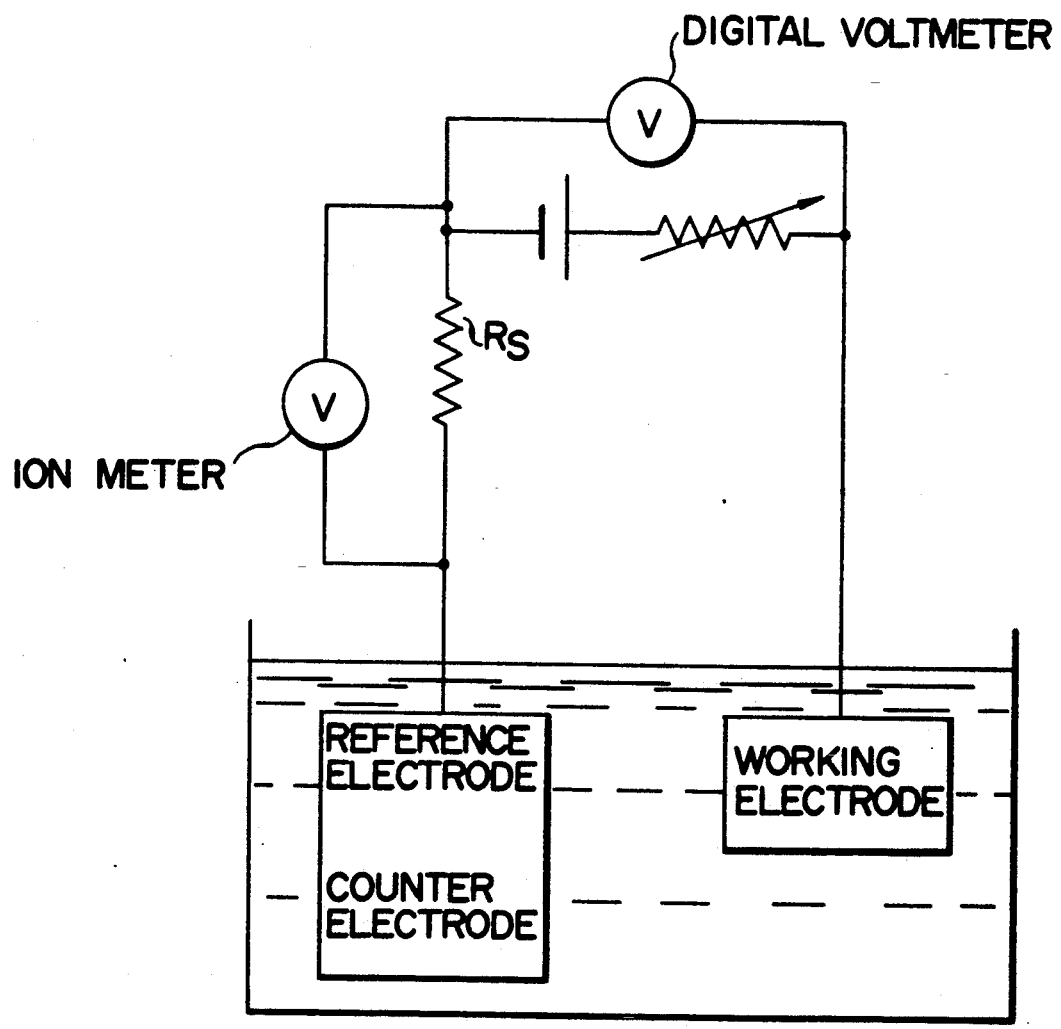
F I G. 27

ION SENSOR

This is a continuation of Application Ser. No. 07/402,969, filed on Sep. 6, 1989, which was abandoned upon the filing hereof Application Ser. Nos. 07/813,516 filed Dec. 26, 1985, 07/029,400 filed Mar. 23, 1987 and 07/168,634 filed Feb. 29, 1988.

BACKGROUND OF THE INVENTION

1. Field of the Invention

The present invention relates to an ion sensor and, more particularly, to an ion sensor of the type wherein an ion concentration in a solution is measured by an electrode potential response.

2. Description of the Prior Art

Conventional ion sensors of the type wherein an ion concentration in a solution is measured by electrode potential response include various ion sensors such as a hydrogen ion sensor, a potassium ion sensor, a calcium ion sensor, a sodium ion sensor, or a chloride ion sensor.

As a hydrogen ion sensor, glass electrodes are widely used, wherein a standard solution having a stable pH and a stable chloride activity is held with an internal reference electrode (Ag/AgCl electrode) in a standard liquid chamber formed by a glass membrane. The sensor is dipped in a sample solution, and the pH value in the sample solution can be measured by the potential difference of both reference electrode between in the internal standard and the outer sample solutions. However, when glass electrodes are used, the glass membrane can be easily damaged or contaminated and their use in alkaline solutions is limited. When a highly viscous solution containing an adsorbing substance (e.g., blood) is to be measured, the measurement precision is degraded within a short period of time. In order to prevent this degradation, substances attached to the glass membrane must be removed every 30 minutes during measurement. In addition, since the glass type electrode has a standard internal solution chamber, it cannot be reduced in size beyond a certain limit.

A pH sensor of the type using a hydrogen ion carrier film in place of a glass membrane is disclosed in, e.g., U.S. Pat. No. 3,743,558, Japanese Patent Disclosure No. 47-7549, and J. Appl. Physiology 40, 14. The hydrogen ion carrier film is obtained by adding a hydrogen ion carrier substance in a polymer film and hydrogen ions from the inner solution permeate the film to reach a reference electrode so as to measure the hydrogen ion concentration. However, in this pH sensor, the carrier film components tend to elute, presenting a problem of poor measurement reproducibility.

As an improvement over this type of pH sensor, a liquid film electrode is reported in Analytica Chimica Acta, 131, 111-116 (1981). A potassium ion sensor using a liquid film electrode is also reported in Analytical Chemistry 46, 2223-2224 (1974). However, both types of sensor have a standard internal solution chamber and cannot be rendered compact in size.

SUMMARY OF THE INVENTION

It is, therefore, an object of the present invention to provide an ion sensor of a solid film type which does not require a standard liquid chamber, wherein a concentration of a specific type of ions is measured by the potential response.

In order to achieve the above object of the present invention, there is provided an ion sensor of the type wherein a specific type of ions in a solution is measured by a potential response, comprising:

a conductor base;

a reversible redox polymer film formed directly on a surface of the conductor base; and an ion carrier film formed directly on a surface of the redox polymer film and containing an ion carrier substance for allowing a specific type of ions to permeate from the aqueous solution to the polymer film.

According to a preferred aspect of the present invention, the reversible redox polymer is derived by electrooxidation polymerization of an amino aromatic compound and/or a hydroxy aromatic compound.

In this specification and claims, the "reversible redox polymer" is intended to indicate polymers having a reversible oxidation/reduction function and include those which undergo an oxidation/reduction reaction of a quinone-hydroquinone type and those which undergo an oxidation/reduction reaction of an amine-quinoid type.

Also, in the specification and claims, the "polymer" includes both a homopolymer and an interpolymer such as a copolymer.

BRIEF DESCRIPTION OF THE DRAWINGS

FIG. 2 is a sectional view showing an ion sensor according to an embodiment of the present invention.

FIGS. 4 to 25 are graphs showing the characteristics of ion sensors according to the present invention.

FIG. 26 is a block diagram showing an apparatus for continuously measuring the hydrogen ion concentration in blood using an ion sensor according to the present invention;

FIG. 27 is a view showing an apparatus used for measuring the electrode resistance of an ion sensor according to the present invention.

DETAILED DESCRIPTION OF THE PREFERRED EMBODIMENTS

The basic structure of an ion sensor according to the present invention will be described with reference to FIG. 1.

Figure 1:
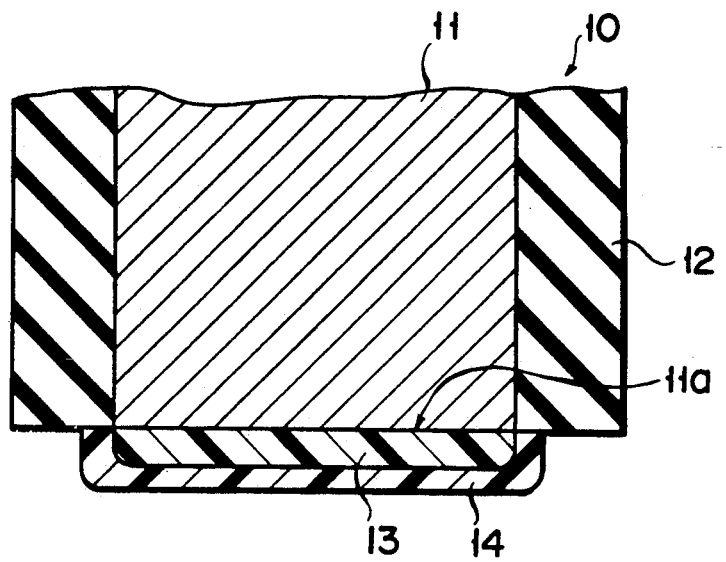
FIG. 1 is a sectional view showing the basic structure of an ion sensor according to the present invention.

As shown in FIG. 1, an ion sensor 10 according to the present invention has an electrically conductive base 11. Although the shape of the base 11 is not particularly limited, it is preferably formed into a thin wire so as to provide a compact sensor. The base 11 can consist of a noble metal such as platinum, gold, silver or palladium, or conductive carbon such as basal plane pyrolytic graphite or glassy carbon. Basal plane pyrolytic graphite (BPG) is particularly preferable as the material of the base 11. A surface portion of the base 11 on which a film having an oxidation/reduction function to be described later is formed can be covered with a semiconductor material such as indium oxide or tin oxide.

The outer surface of the base 11, except for its end faces, is covered with an insulating material 12 such as teflon.

A solid film 13 of a reversible redox polymer is directly formed on an end face 11a of the base 11. When a specific type of ions in an aqueous solution permeate an ion carrier film 14 to be described later, the solid film 13 undergoes the reversible oxidation/reduction reaction and generates a specific potential in the conductive base 11. The specific potential generated in the base 11 in this manner corresponds to the ion concentration. The oxidation/reduction reactions of the redox polymer films are the reversible oxidation/reduction reaction of quinone-hydroquinone type represented by the general formula:

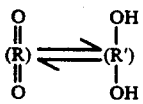

(wherein R and R' are polymer structures), and the reversible oxidation/reduction reaction of an amine-quinoid type represented by the general formula:

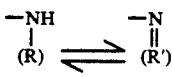

(wherein R and R' are polymer structures).

Compounds capable of forming redox polymers which undergo the oxidation/reduction reaction of a quinone-hydroquinone type include hydroxy aromatic compounds and nonhydroxy quinone compounds.

The hydroxy aromatic compounds can be represented by general formula (I):

$$\begin{matrix} (OH)_m \\ | \\ Ar\text{———}(R^0)_n \end{matrix} \quad (I)$$

(wherein Ar is an aromatic nucleus, each $R^0$ is a substituting group, m is 1 to an effective valency of Ar, and n is 0 to (effective valency of Ar−1). The aromatic nucleus Ar can be a monocyclic ring such as a benzene nucleus, a polycyclic ring (condensed ring) such as an anthracene nucleus, a pyrene nucleus, a chrysene nucleus, a perylene nucleus, or a coronene nucleus, or a heterocyclic ring. The substituting group $R^0$ can be an alkyl group such as methyl group, an aryl group such as phenyl group, and a halogen atom. Examples of the hydroxy aromatic compounds may include phenol, 3,5-, 2,6- and 3,4-xylenols, 2-hydroxypyridine, o- and m-benzylalcohols, o-, m- and p-hydroxybenzaldehydes, o-, m- and p-hydroxyacetophenones, o-, m- and p-hydroxypropiophenones, o-, m- and p-benzophenols, o-, m- and p-hydroxybenzophenones, o-, m- and p-carboxyphenols, diphenylphenol, 2-methyl-8-hydroxyquinoline, 5-hydroxy-1,4-naphthoquinone, 4-(p-hydroxyphenyl)-2-butanone, 1,5-dihydroxy-1,2,3,4-tetrahydronaphthalene, bisphenol A, salicylanilide, 5- and 8-hydroxyquinolines, 1,8-dihydroxyanthraquinones, 1,2,5,8-tetrahydroxyquinalizarin, and 1-amino-4-hydroxyanthraquinone.

Examples of the quinone compound containing no hydroxyl group may include 1,6-pyrenequinone, phenanthrenequinone, 1-aminoanthraquinone, purpurin, and anthrarufin.

The compounds for forming redox polymer films capable of the oxidation/reduction reaction of amine-quinoid type are aromatic primary amines represented by the following general formula (II):

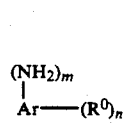

(wherein Ar, $R^0$, m and n have the same meanings as in formula (I) above). Examples of such aromatic primary amines may include aniline, 1-aminopyrene, 1,2-, 1,6- and 1,8-diaminopyrenes, 1-aminochrysene, 1,4-diaminochrysene, 1- and 9-aminophenanthrenes, 9,10-diaminophenanthrenes, 1-aminoanthraquinone, p-phenoxyaniline, o-phenylenediamine, p-chloroaniline, 3,5-dichloroaniline, 2,4,6-trichloroaniline, and N-phenyl-p-phenylenediamine. In addition, aromatic secondary amines such as N-methylaniline may also be used.

The hydroxy aromatic compounds, amino-containing compounds and quinone compounds as described above may be referred to as monomers herein. Among these monomers, 2,6-xylenol and 1-aminopyrene are particularly preferable.

Redox polymer films of at least one monomer selected from those enumerated above can be formed on the end faces 11a of the base 11 by various methods. According to one method, a selected monomer is directly polymerized on the surface of the base 11 by electrooxidation polymerization or electrolytic precipitation. According to another method, a selected monomer is polymerized by irradiation with an electron beam or light or by application of heat. The base 11 is dipped in a solution obtained by dissolving the resultant polymer in a solvent, and drying coated polymer. According to still another method, a polymer is prepared and is directly fixed on the surface of the base 11 by chemical, physical or radiation treatment. Among these methods, the method of directly coating a redox polymer by electrooxidation polymerization is preferable.

In order to perform electrooxidation polymerization, at least one type of monomer is dissolved in a solvent containing a supporting electrolyte. The base 11 and a reference electrode, e.g., a sodium chloride saturated calomel electrode (SSCE) are dipped in the resultant solution. When a voltage is applied to the base (normally, +1.0 to +1.5 V vs. SSCE), electrooxidation polymerization of the monomer takes place to precipitate a film. Examples of the solvent which may be used in such electrooxidation polymerization may include acetonitrile, water, dimethylformamide, dimethylsulfoxide, and propylene carbonate. Examples of the supporting electrolyte may include sodium perchlorate, sulfuric acid, sodium sulfate, boric acid, tetrafluoro potassium phosphate, and quaternary ammonium salts. Electrooxidation polymerization is preferably performed by adding a catalytic amount (e.g., 1 mM to 100 mM, preferably 10 to 30 mM) of pyridine.

A redox polymer derived by electrooxidation polymerization is dense and does not allow permeation of oxygen molecules even if the polymer film is thin.

The redox polymer film 13 does not preferably change its potential depending upon the partial oxygen gas content in an aqueous solution. A redox polymer derived from any of the monomers enumerated above has this property.

The redox polymer film 13 preferably has a thickness of 0.1 μm to 0.2 mm. When the film thickness is smaller than 0.1 μm, desired redox properties are not obtained. If the film thickness exceeds 0.2 mm, the film resistance is undesirably increased.

The redox polymer film according to the present invention can be impregnated with an electrolyte. When the film is impregnated with an electrolyte, the charge transfer rate of the film is increased, the film resistance is reduced and conductivity of the film is increased. When a suitable electrolyte for impregnation is selected, the charge transfer resistance at the interface between the redox polymer film and the carrier film can be decreased. Dissolution diffusion of the redox polymer in the carrier film can also be prevented.

Examples of the electrolyte for impregnation of the redox polymer may include phosphoric acid, dipotassiumhydrogenphosphate, sodium perchlorate, sulfuric acid, tetrafluoroborate, and tetraphenylborate. In order to impregnate the redox polymer with an electrolyte, after the redox polymer is coated on the surface of the base 11, the base 11 is dipped in a solution of the selected electrolyte. The electrolyte is impregnated in an amount by weight of about $10^{-6}$ to $10^{-1}$ based on the weight of the redox polymer film. The impregnation amount is preferably $10^{-3}$ to $10^{-1}$.

An ion carrier film 14 containing an ion carrier substance for selectively carrying a specific type of ions (e.g., the type of ions whose concentration is to be measured) in an aqueous solution to the surface of the redox polymer film is formed on the surface of the redox polymer film 13.

The ion carrier film 14 consists of a film forming polymeric material and an ion carrier substance.

The ion sensor of the present invention constitutes a sensor of ions of a type in accordance with the type of ion carrier substance contained in the film 14. For example, when a hydrogen ion carrier substance is used, a hydrogen ion sensor is obtained. Similarly, a potassium ion sensor is obtained with a potassium ion carrier substance, a sodium ion sensor with a sodium ion carrier substance, a calcium ion sensor with a calcium ion carrier substance, a chloride ion sensor with a chloride ion carrier substance, and a hydrogencarbonate ion sensor with a hydrogencarbonate ion carrier substance.

Examples of the hydrogen ion carrier substance may include alkylamines represented by:

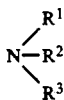
(A)

(wherein each of $R^1$, $R^2$ and $R^3$ is an alkyl group, at least two of which are alkyl groups having 8 to 18 carbon atoms and preferably 10 to 16 carbon atoms), and pyridine derivatives represented by:

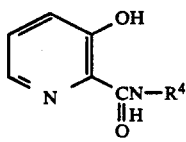
(B)

(wherein $R^4$ is an alkyl group having 8 to 18 carbon atoms and preferably 10 to 16 carbon atoms).

Examples of the amine represented by the general formula (A) may include tri-n-dodecylamine, tri-n-decylamine, tri-n-octylamine, di-n-dodecyl-n-decylamine, and di-n-todecyl-n-octylamine.

Examples of the amine represented by the general formula (B) may include 3-hydroxy-N-dodecyl-picolineamine, 3-hydroxy-N-decylpicolineamine, and 3-hydroxy-N-octyl-picolineamide.

Tridodecylamine and 3-hydroxy-N-dodecyl-picolineamide is preferable as a hydrogen ion carrier substance.

Examples of the potassium ion carrier substance may include valinomycin, bis(crown ether) (e.g. bis[(benzo-15-crown-5)-4'-methyl]pimelate, bis[(benzo-15-crown-5)-4'-methyl]oxide), nonactin, monactin, and crown ethers (e.g., dibenzo-18-crown-6, dibenzo-15-crown-5, dibenzo-30-crown-10, and dicyclohexyl-18-crown-6). Valinomycin and bis[(benzo-15-crown-5)-4'-methyl]pimelate are particularly preferable.

Examples of the sodium ion carrier substance may include bis[(12-crown-4)methyl]dodecylmalonate, N,N,N,N,-tetrapropyl-3,6-dioxanate-diamide, 3-methoxy-N,N,N,N-tetrapropyl-1,2-phenylenedioxydiacetoamide, (−)-(R,R)-4,5-dimethyl-N,N,N,N-tetrapropyl-3,6-dioxaoctanediamide, 4-methyl-N,N,N,N-tetrapropyl-3,6-dioxaoctanediamide, N,N,N,N-tetrapropyl-1,2-phenylenedioxydiacetoamide, N,N,N,N-tetrapropyl-2,3-naphtharenedioxydiacetoamide, 4-t-butyl-N,N,N,N-tetrapropyl-1,2-cyclohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide. Bis[(12-crown-4)methyl]dodecylmalonate is particularly preferable.

Examples of the calcium ion carrier substance may include calcium-bis- di-(n-octylphenyl) phosphate, (−)-(R,R)-N, N'-bis[(11-ethoxycarbonyl)undecyl]-N,N'-4,5-tetramethyl-3,6-dioxaoctanediamide, and calcium[bis di(n-decyl)phosphate]. Calcium-bis[di(n-octylphenyl) phosphate] is particularly preferable.

Examples of the chloride ion carrier substance may include quaternary ammonium salts represented by the general formula:

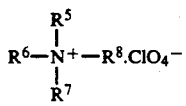
(C)

(wherein each of $R^5$, $R^6$, $R^7$ and $R^8$ is independently an alkyl group having 6 to 18 carbon atoms, and one of $R^5$ to $R^8$ can contain a hydrogen atom or a methyl group), and triphenyl tin chloride represented by:

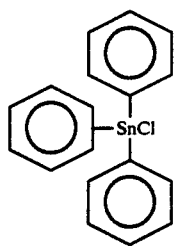

Examples of the quaternary ammonium salts represented by general formula (C) above may include tetraoctylammonium perchlorate, methyltri-n-decylammonium perchlorate, methyltri-n-dodecylammonium perchlorate, methyltri-octylammonium perchloride, methyltri-n-ammonium perchlorate, and n-tetrahexylammonium perchlorate. Particularly preferable chlorine ion carrier substances are tetraoctylammonium perchlorate, methyltri-n-decylammonium perchlorate, and methyltri-dodecylammonium perchlorate.

Examples of the hydrogencarbonate ion carrier substance may include a quaternary ammonium salt of the formula:

where $R^9$ to $R^{11}$ are independently alkyl groups having 8 to 18 carbon atoms and $X^-$ is $Cl^-$, $Br^-$ or $OH^-$; a tertiary amine of the formula

where $R^{12}$ is phenyl group, methyl group or hydrogen atom, $R^{13}$ is hydrogen atom or methyl group, and $R^{14}$ is hydrogen atom, methyl group or octadecyl group; and the compounds of formulas:

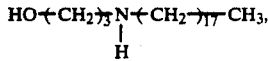

and

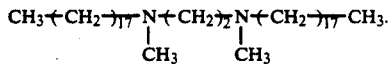

Each ion carrier substance is preferably used in an amount of 0.1 to 15.0 parts by weight based on 100 parts by weight of the ion carrier film.

The ion carrier film conveniently contains an electrolyte salt in addition to an ion carrier substance. An electrolyte salt serves to enhance the ion transfer in a plasticizer solution. A second effect of the electrolyte salt increases the conductivity of the carrier and decreases the film resistance, and prevents permeation of charges of opposite polarity in the solution to the film.

Examples of the electrolyte salt contained in the ion carrier film may include sodium tetrakis(p-chlorophenyl)borate, potassiumtetrakis(p-chlorophenyl)borate; and compounds represented by general formulas:

and

(wherein each $R^{15}$ is independently an alkyl group and preferably an alkyl group having 2 to 6 carbon atoms). Examples of the compound represented by general formula (F) may include compounds wherein $R^{15}$ is an alkyl group having 1 and 10 carbon atoms. At least one of tetraalkyls can be a methyl group. Examples of the compound represented by general formula (G) may be compounds wherein $R^{15}$ is an alkyl group having 1 and 10 carbon atoms. At least one of tetraalkyls can be a methyl group. An electrolyte salt is preferably contained in an amount of 0.05 to 3.0 parts by weight in the ion carrier film.

The polymeric material of the film 14 carries an ion carrier substance and an electrolyte salt and fixes them to the redox polymer film 13. The polymeric material must be able to form a film. Examples of such a polymeric material may include polyvinyl chloride, a vinyl chloride-ethylene copolymer, polyester, polyacrylamide, polyurethane, and silicone resin. Such a polymeric material, in particular, polyvinyl chloride may be mixed with a plasticizer such as dioctyl sebacate, dioctyl maleate, dioctyl adipate, and bis(2-ethylnexyl) sebacate.

Among these polymeric materials, polyvinyl chloride is preferable due to high film formability. Polyvinyl chloride is preferably in a paste form. Paste polyvinyl chloride stably carries an ion carrier substance and firmly adheres to the surface of the base without separation. Paste polyvinyl chloride has a short solidification time of 5 minutes or less and allows easy film formation. Paste polyvinyl chloride is obtained by adding 50 to 500 parts by weight of a plasticizer to 100 parts by weight of polyvinyl chloride.

In order to form an ion carrier film on the redox polymer film 13, a polymeric substance, ion carrier substance, an electrolyte, and a plasticizer, if required, are dissolved in a solvent, e.g., tetrahydrofuran. The base having the redox polymer film is dipped in the solution and the film is dried.

As will be described later, an ion sensor according to the present invention has an electromotive force (E) generated in the conductive base 11 which linearly changes in accordance with the concentration of a specific type of ions in an aqueous solution. The linear relationship between the E value and the ion concentration (e.g., pH value in the case of hydrogen ions), more specifically, the slope (e.g., mV/pH) of the line is more approximate to the theoretical value (59.16 mV at 25° C.) when the film 14 has a larger thickness. Normally, the film 14 has a thickness of 200 μm to 10 mm. Changes in electromotive force with a thickness falling within this range are small. The response time (time required for the electromotive force to reach a predetermined value) is slightly prolonged as the thickness of the ion carrier film is increased. However, no actual problem is encountered if the thickness of the film 14 remains within the above range. When the thickness of the film 14 remains within this range, the response time is very short. A film resistance R of the film 14 increases proportionally to an increase in the film thickness (in accordance with the Ohm's law). The resistance R also has a correlation with an area S of the base on which the film 14 is formed ($R = \rho = d/S$). When the film resistance is taken into consideration (low resistance is preferred), the ion carrier film 14 particularly preferably has a thickness of 300 μm to 1 mm.

FIG. 2 shows the detailed construction of the ion sensor according to the present invention. As shown in FIG. 2, a redox polymer film 23 is formed on one end face 21a of a base 21 of a conductive material. The base 21 is inserted into an insulating tube 22a such that one end 21a of the base 21 coincides with that of the tube 22a. The base 21 is a wire having a diameter of, e.g., 0.25 to 5.0 mm. A leading wire 27 is connected to the other end 21b of the base 21 by a conductive adhesive 25. An insulating resin 22b is filled in the tube 22a including the gap between the base 21 and the tube 22a. An insulating tube 26 covers the tube 22a so as to project from the base 21. An ion carrier film 24 is formed on the projecting portion of the tube 26 so as to be in direct contact with the redox polymer film.

Figure 3:
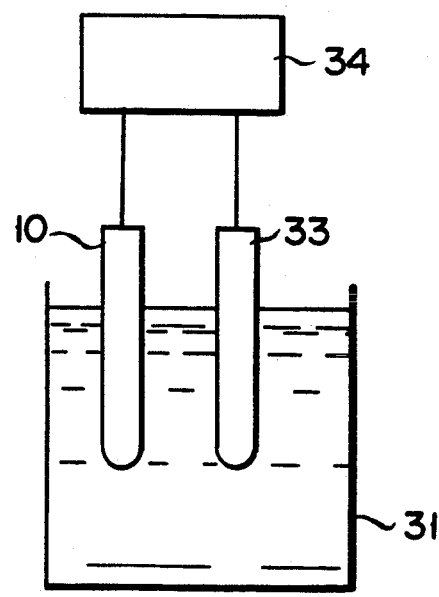
FIG. 3 is a view for explaining the principle of measuring a concentration of a specific type of ions in an aqueous solution using an ion sensor according to the present invention.

In order to measure a concentration of a specific type of ion in an aqueous solution using an ion sensor of the present invention as described above, as shown in FIG. 3, an ion sensor 10 of the present invention is dipped together with a reference electrode 33 such as a saturated calomel electrode in an aqueous solution 32 to be measured held in a container 31. The ion sensor 10 and the reference electrode 33 are connected to a potentiometer 34. The specific type of ions in the solution are immediately permeated to a redox polymer film 13 through an ion carrier film 14. The film 13 undergoes the oxidation/reduction reaction and generates an electromotive force corresponding to the concentration of the specific type of ions. The electromotive force generated is measured by the potentiometer 34 as a difference with respect to the reference electrode 33. The electromotive force of the ion sensor of the present invention has a linear relation (Nernst equation) with the ion concentration. Thus, the concentration of the specific type of ions in the solution can be measured.

The present invention will now be described by way of its Examples.

EXAMPLE 1

A surface of a disk (diameter: 5 mm; length: 5 mm) consisting of basal plane pylolytic graphite (BPG) was cleaved by a sharp cutter to expose a new surface. The outer circumferential surface of the disk base was covered with a heat shrinkable tube for insulation, and mercury was charged into the tube to connect the base and a leading wire. This BPG disk was used as a working electrode, a saturated sodium chloride calomel electrode (SSCE) was used as a reference electrode, and a platinum net was used as a counter electrode. Electrooxidation polymerization was performed in a three electrode electrolysis cell under the conditions presented below so as to form an electrooxidation polymer film on the exposed surface of the base.

An electrolytic solution was obtained by adding 10 mM/l of 1-aminopyrene (AP) and 10 mM/l of pyridine to an acetonitrile solvent containing 0.1 M/l of sodium perchlorate as a supporting electrolyte. After sweeping the potential of the working electrode at a speed of 50 mV/sec within a range of 0 V to +1.0 V (with reference to the SSCE) three times, constant potential electrolysis was performed at +1.0 V (with reference to the SSCE) for 10 minutes. Thus, an electrooxidation polymer film (oxidation/reduction film) of 1-aminopyrene was formed on the surface of the base. The polymer film was rinsed with water and was stored in a phosphate buffer solution, having a pH of 6.86, for one day so as to stabilize the oxidation/reduction potential of the oxidation/reduction film. After the oxidation/reduction film was dried, a hydrogen ion carrier film was formed by the following method.

25.6 mg of tri-n-dodecylamine, 5.7 mg of potassium-tetrakis(p-chlorophenyl) borate, 732 mg of dioctylsebacate, and 367 mg of polyvinyl chloride (average polymerization degree of 1,050) were dissolved in 10 ml of tetrahydrofuran. The base with the oxidation/reduction film was dipped in the solution, and the solvent was removed by drying so as to form a hydrogen ion carrier film on the oxidation/reduction film. The pH sensor of the present invention was prepared in this manner.

TEST EXAMPLES 1-6

Figure 4:
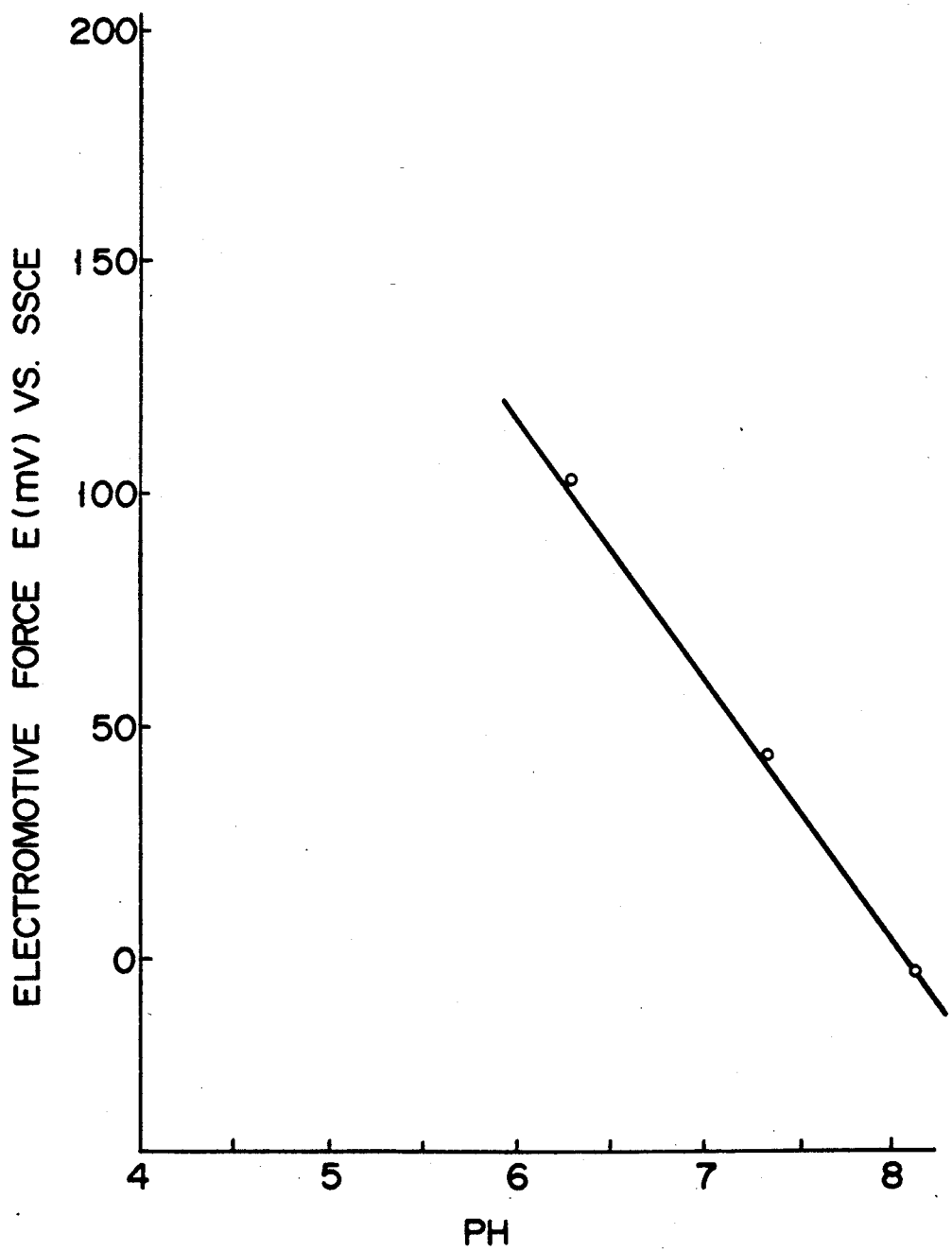
Figure 5:
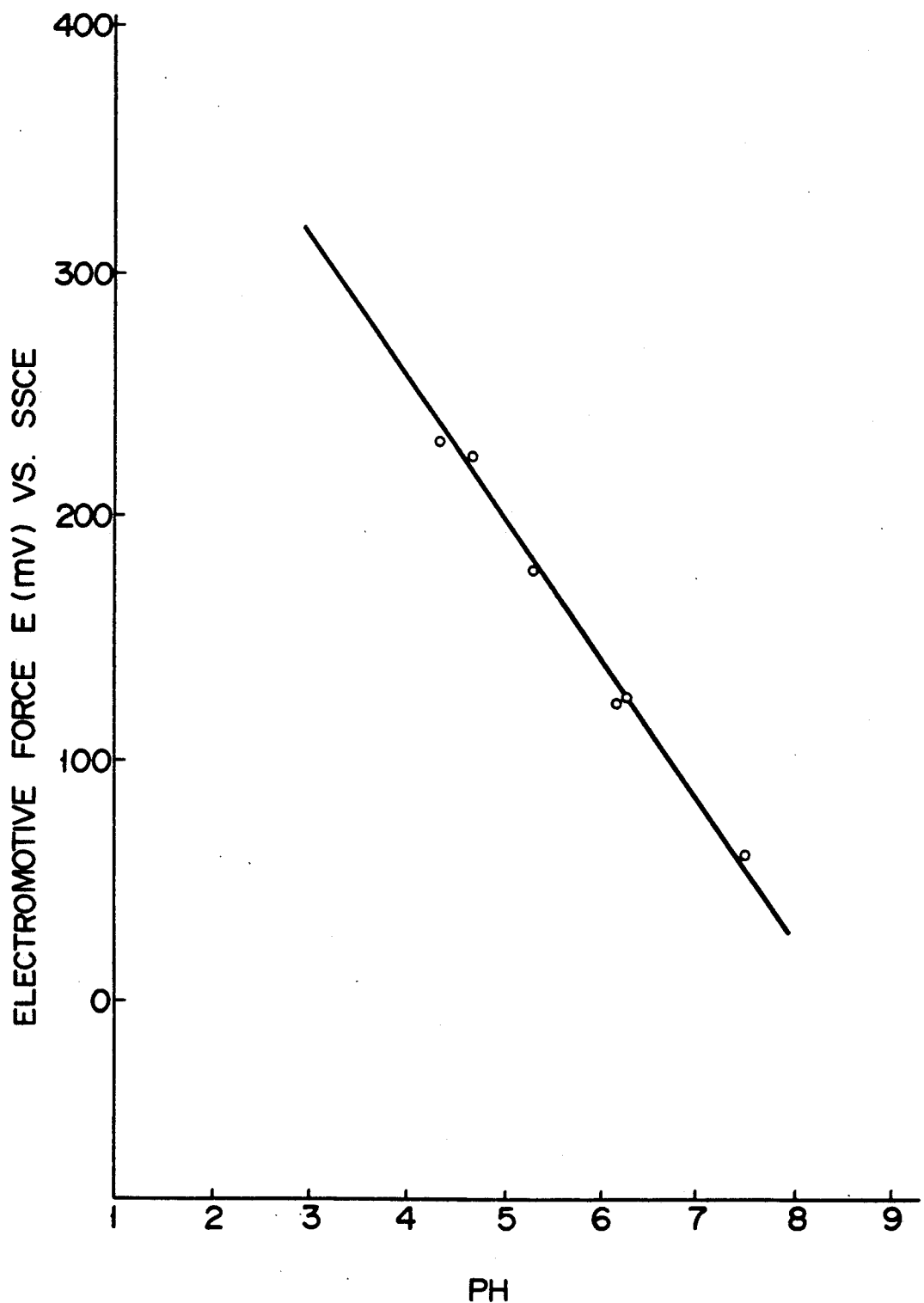
Figure 6:
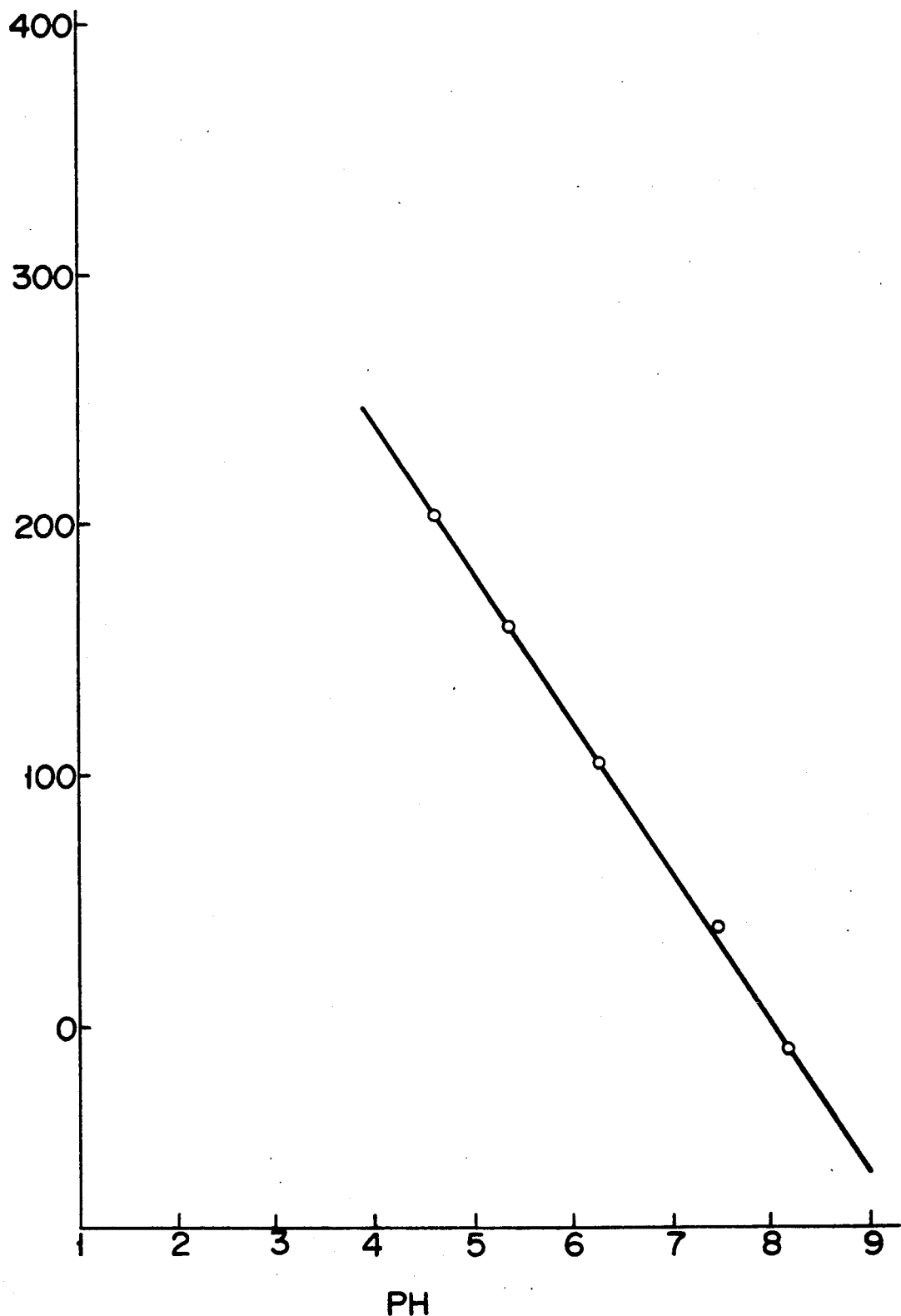

The equilibrium potentials obtained by the sensor in each different solution and the pH were measured using the pH sensor prepared in Example 1 and an SSCE as a reference electrode. The solutions measured were cow's blood (Test Example 1), standard serum (Versatol A, General Giagotics der Werner-Lambert Inc.) (Test Example 2), a lactic acid Ringer solution (composition: 0.6% (w/v) of sodium chloride, 0.03% (w/v) of potassium chloride, and 0.31% (w/v) of lactic acid; electrolyte components: 131 mg/l of $Na^+$, 4 mg/l of $K^+$, 3 mg/l of $Ca^{2+}$, 110 mg/l of Cl, and 28 mg/l of lactate) (Test Example 3), a solution obtained by adding 5% (w/v) of dextran to 0.1 M/l physiological saline solution (Test Example 4), a bioelectrolyte solution ("HICALIQ" available from TERUMO; composition: dextrose, potassium acetate, calcium gluconate, magnesium sulfate, $KH_2PO_4$, $ZnSO_4 7H_2O$, and electrolyte ions $K^+$ (25 mg), $Mg^+$ (8.5 mg), $Ca^{2+}$ (150 mg) and $SO_4^{2-}$ (10 $\mu M$) (Test Example 5), and artifical urine ("Urine Control 1" available from UR Sure Chemistry). (Test Example 6). The obtained results are shown in FIG. 4 (Test Example 1), FIG. 5 (Test Examples 2, 5) and FIG. 6 (Test Examples 3 and 4).

TEST EXAMPLE 7

Figure 7:
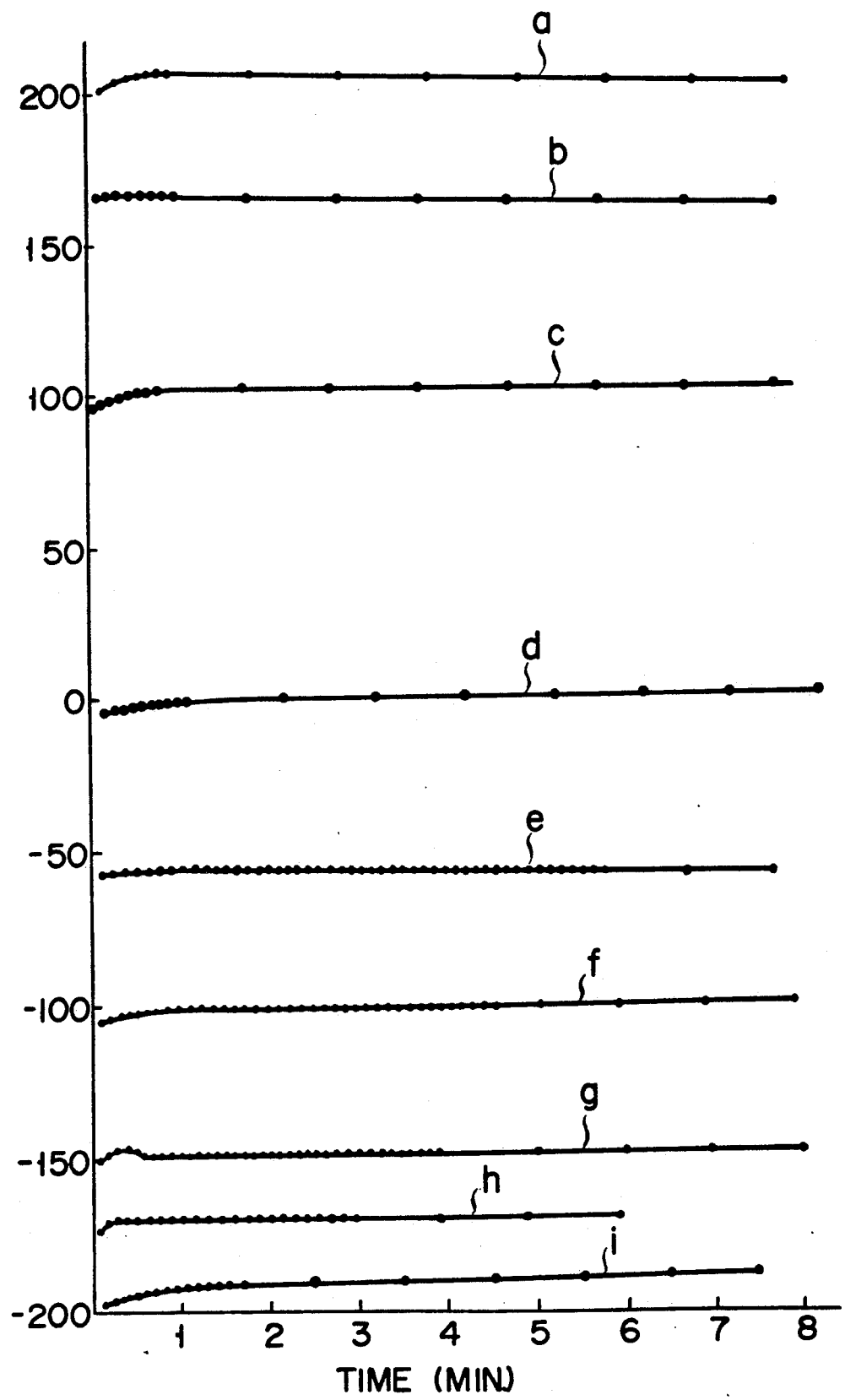

Using the pH sensor prepared in Example 1, response times (time required to achieve an equilibrium potential) at 25° C. were measured when the pH of the solution was changed with a phosphate buffer solution from 5.34 to 4.67 (a), 7.46 to 5.34 (b), 4.67 to 6.27 (c), 6.27 to 8.16 (d), 8.16 to 9.18 (e), 9.18 to 10.02 (f), 10.02 to 11.0 (g), 11.0 to 12.0 (h) and 12.0 to 13.0 (i), respectively. The results indicated extremely fast responses of from 20 seconds to 2 minutes as indicated by lines a to i in FIG. 7. The electrode potential was stable after 8 days.

TEST EXAMPLE 8

The change in electromotive force per pH of the pH sensor prepared in Example 1, i.e., the slope (mV/pH) of the linear Nernst equation was measured while changing the temperature of the solution. For the purpose of comparison, the slope of the line for a pH sensor (Comparative Example) in which no hydrogen carrier film was used and a glass electrode was similarly measured. The obtained results are shown in Table 1. It is seen from the obtained results that the pH sensor of the present invention provides a similar effect to that of a glass electrode and that therefore the pH sensor of the present invention can be used in a measurement system using a glass electrode.

TABLE 1

| Measurement Temperature | Slope of Line (mV/pH) | | | |
| --- | --- | --- | --- | --- |
| | pH Sensor of Example 1 | Comparative Example | Glass Electrode | Theoretical Value (Nernst Equation) |
| 4.5 | — | 49 | 53.0 | 55.09 |
| 10.0 | 56.0 | — | 56.0 | 56.19 |
| 25.0 | 59.0 | 46 | 59.0 | 59.16 |
| 37.0 | 60.5 | 47 | 61.0 | 61.75 |
| 50.0 | 64.0 | 51 | 64.0 | 64.12 |

TEST EXAMPLE 9

The influence of the oxygen partial pressure on the equilibrium potential was measured using the pH sensor prepared in Example 1 and changing the oxygen partial pressure within a range of 47 mmHg to 630 mmHg with a standard phosphate buffer solution having a pH of 6.86. The measurement temperature was 37° C.±0.1° C.

Figure 8:
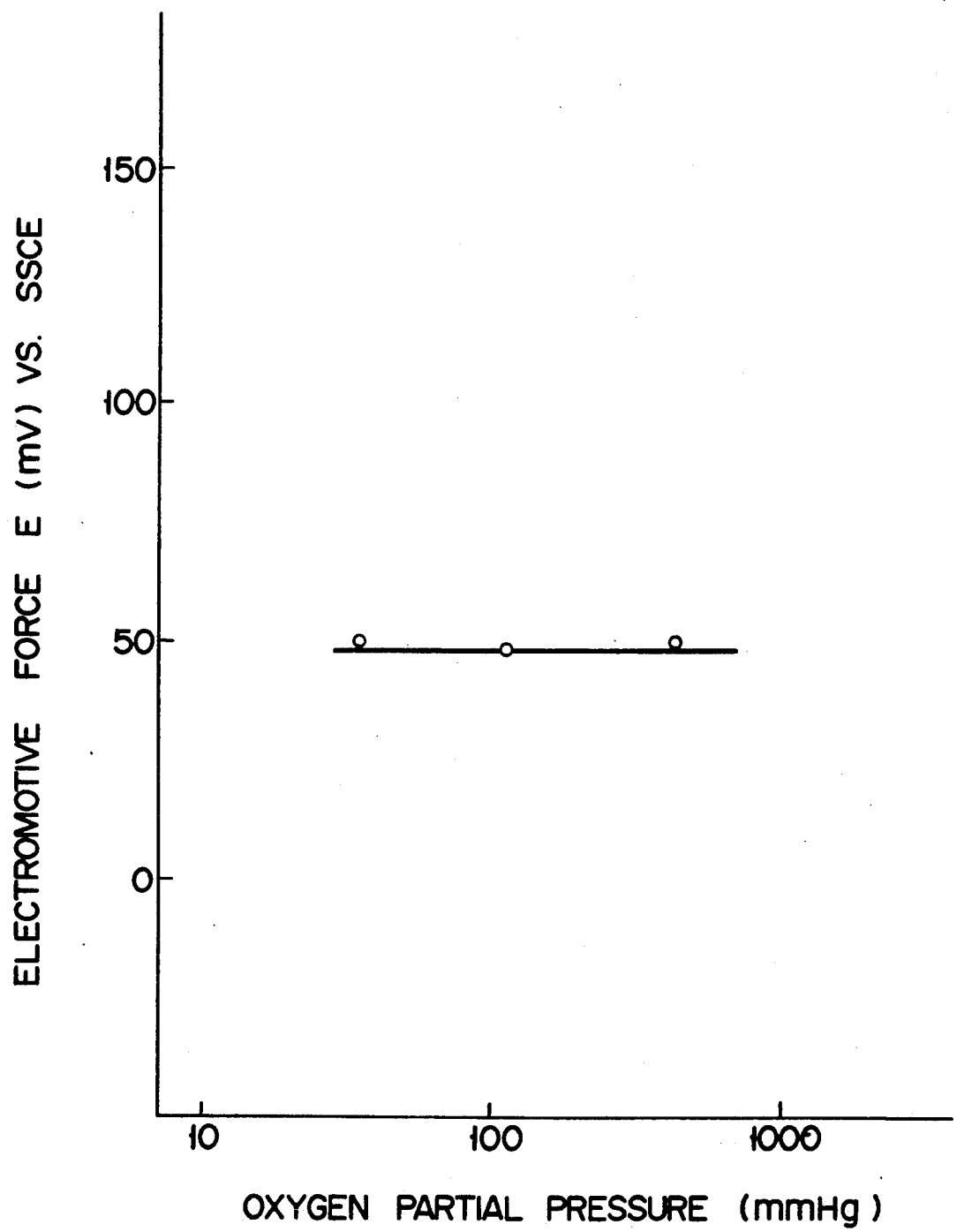

The obtained results are shown in FIG. 8. It is seen from these results that the pH sensor is not affected by the oxygen partial pressure.

EXAMPLE 2

A pH sensor was prepared following the same procedures as in Example 1 except that tetrabutylammonium tetrafluoroborate was used in place of sodium perchlorate as a supporting electrolyte.

TEST EXAMPLE 10

When the relationship between the electromotive force generated by the pH sensor prepared in Example 2 and the pH was examined (37° C.), a linear relation was obtained. The line had a slope of 58 mV/pH. The electromotive force at pH 7.4 was about 40 mV.

EXAMPLES 3 AND 4

A pH sensor was prepared following the same procedures as in Example 1 except that carbon fiber ("HTA-7W-100" available from Toho Rayon; resistibility: about $1.5 \times 10^{-3}$ Ω·cm; cross-sectional area: $3.8 \times 10^{-4}$ cm$^2$) was used in place of basal plane pyrolytic graphite (Example 3). Another pH sensor was similarly prepared by using BPG having a diameter of 0.5 mm (Example 4).

TEST EXAMPLE 11

When the relationship between the equilibrium potential and the pH for each of the pH sensors of Examples 3 and 4 was tested, it yielded a linear relation. The respective lines had slopes of 62 mV/pH and 60 mV/pH. pH measurement could be performed in other solutions used in

TEST EXAMPLES 1 TO 6

EXAMPLE 5

A pH sensor was prepared following the same procedures as in Example 1 except that 1-aminoanthracene was used in place of 1-aminopyrene.

TEST EXAMPLE 12

When the relationship between the equilibrium potential of the pH sensor prepared in Example 5 and the pH of the solution was examined, it provided a linear relation. The line had a slope of 56 mV/pH within a pH range of 5.15 to 8.20.

EXAMPLE 6 AND 7 pH ion sensors were prepared following the same procedures except that trioctylamine (Example 6) and tridecylamine (Example 7) were used in place of tri-n-dodecylamine when a hydrogen ion carrier film was coated.

TEST EXAMPLE 13

When the relationship between the equilibrium potential of the pH sensor prepared in each of Examples 6 and 7 and the pH of the solution was tested, it provided a linear relation. Each line had a slope of 56 mV/pH. A linear relation was also obtained when artificial urea was used in place of a phosphate buffer solution as a measurement solution.

EXAMPLES 8–11 pH sensors were prepared following the same procedures as in Example 1 except that platinum (Example 8), palladium (Example 9), indium oxide (Example 10), and silver (Example 11) were used in place of BPG for bases and electrooxidation polymerization was performed under the conditions indicated in Table 2 below.

TABLE 2

| Example | Base Material | Surface Area (cm$^2$) | Supporting Electrolyte | Solvent | AP | Pyridine |
|---|---|---|---|---|---|---|
| 8 | Platinum | $1.96 \times 10^{-3}$ | 0.1M NaClO$_4$ | Acetonitrile | 10 mM | 10 mM |
| 9 | Palladium | $1.96 \times 10^{-3}$ | 0.1M NaClO$_4$ | Acetonitrile | 10 mM | 0 |
| 10 | Indium oxide | $1.6 \times 10^{-3}$ | 0.1M TABF$_4$ | Acetonitrile | 10 mM | 10 mM |
| 11 | Silver | $1.96 \times 10^{-3}$ | 0.1M NaClO$_4$ | Acetonitrile | 10 mM | 10 mM |

TEST EXAMPLE 14

When the relationship between the equilibrium potential of the pH sensor prepared in each of Examples 8 to 11 and the pH of the solution was examined (25° C.), it yielded a linear relation. The slope of each line and other results are shown in Table 3 below:

TABLE 3

| pH Sensor Example No. | Slope of Line (mV/pH) | pH Region | Electromotive Force (mV) At pH 6.86 (vs. SSCE) |
|---|---|---|---|
| 8 | 54 | 4–8.5 | 340 |
| 9 | 54 | 4–8.5 | 192 |
| 10 | 57 | 4–8.5 | 192 |
| 11 | 59 | 4–8.5 | 198 |

EXAMPLE 12

A pH sensor was prepared following the same procedures as in Example 1 except that sodium sulfate or sulfuric acid of 0.5M concentration containing 10 mM p-phenoxyaniline as an electrolyte was used for electrooxidation polymerization.

TEST EXAMPLE 15

When the relationship between the equilibrium potential of the pH sensor prepared in Example 12 and the pH of the solution was examined, it yielded a linear relation. The line had a slope of 54 mV/pH. When the pH was 6.86, the equilibrium potential was about 62 mV and the response time was about 1 minute.

EXAMPLES 13–32 pH electrodes were prepared following the same procedures as in Example 1 except that AP electrooxidation polymerization was performed under the conditions shown in Table 4 below:

TABLE 4

| Example | eyridine Content (mM) | Supporting Electrolyte | Solvent |
| --- | --- | --- | --- |
| 13 | 0 | 0.1M NaClO$_4$ | Acetonitrile |
| 14 | 5 | 0.1M NaClO$_4$ | Acetonitrile |
| 15 | 10 | 0.1M NaClO$_4$ | Acetonitrile |
| 16 | 50 | 0.1M NaClO$_4$ | Acetonitrile |
| 17 | 100 | 0.1M NaClO$_4$ | Acetonitrile |
| 18 | 0 | 0.1M TBABF$_4$ | Acetonitrile |
| 19 | 5 | 0.1M TBABF$_4$ | Acetonitrile |
| 20 | 10 | 0.1M TBABF$_4$ | Acetonitrile |
| 21 | 50 | 0.1M TBABF$_4$ | Acetonitrile |
| 22 | 100 | 0.1M TBABF$_4$ | Acetonitrile |
| 23 | 0 | 0.1M NaClO$_4$ | Tetrahydrofuran |
| 24 | 5 | 0.1M NaClO$_4$ | Tetrahydrofuran |
| 25 | 10 | 0.1M NaClO$_4$ | Tetrahydrofuran |
| 26 | 50 | 0.1M NaClO$_4$ | Tetrahydrofuran |
| 27 | 100 | 0.1M NaClO$_4$ | Tetrahydrofuran |
| 28 | 0 | 0.1M TBABF$_4$ | Tetrahydrofuran |
| 29 | 5 | 0.1M TBABF$_4$ | Tetrahydrofuran |
| 30 | 10 | 0.1M TBABF$_4$ | Tetrahydrofuran |
| 31 | 50 | 0.1M TBABF$_4$ | Tetrahydrofuran |
| 32 | 100 | 0.1M TBABF$_4$ | Tetrahydrofuran |

TEST EXAMPLES 16-35

Figure 9:
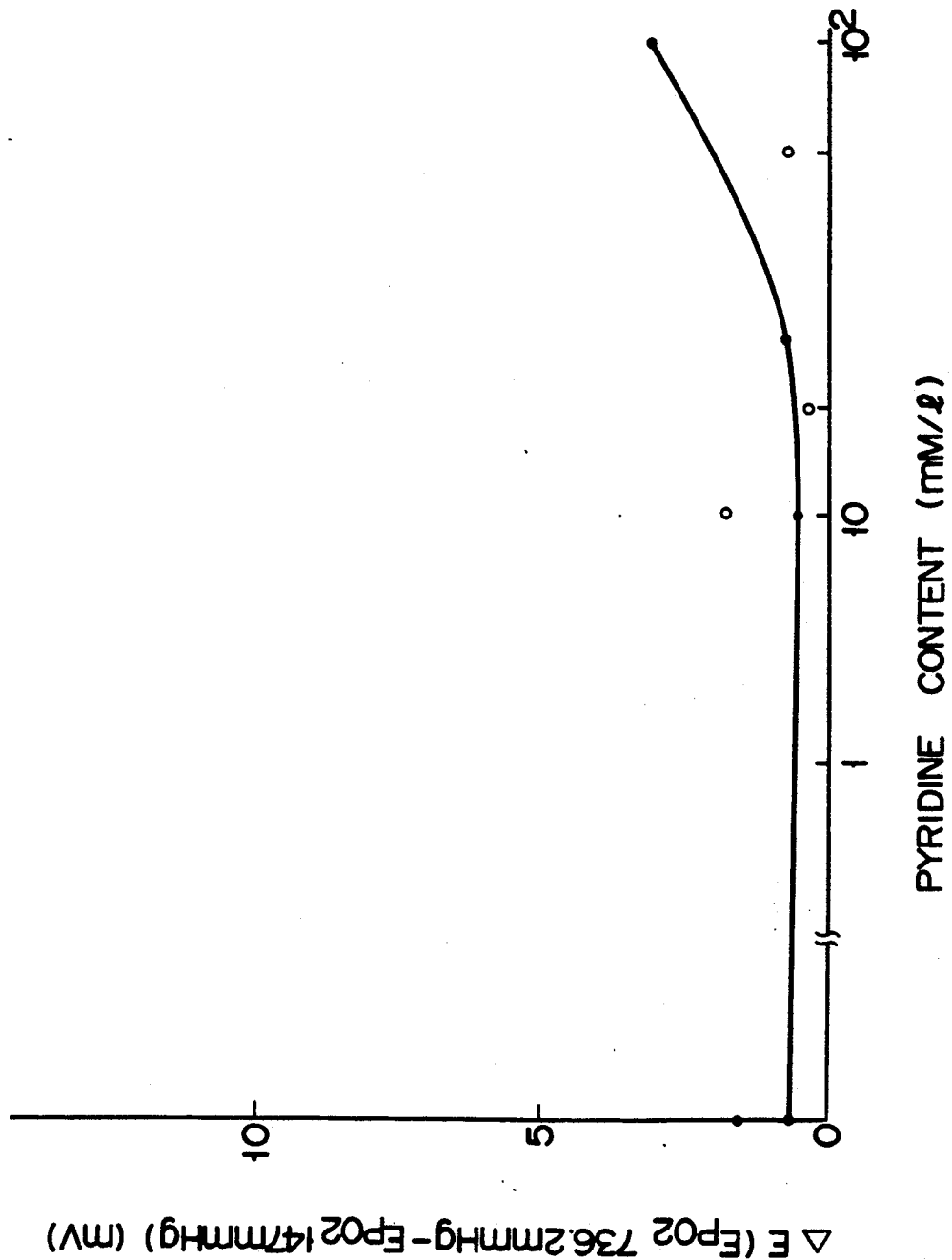
Figure 10:
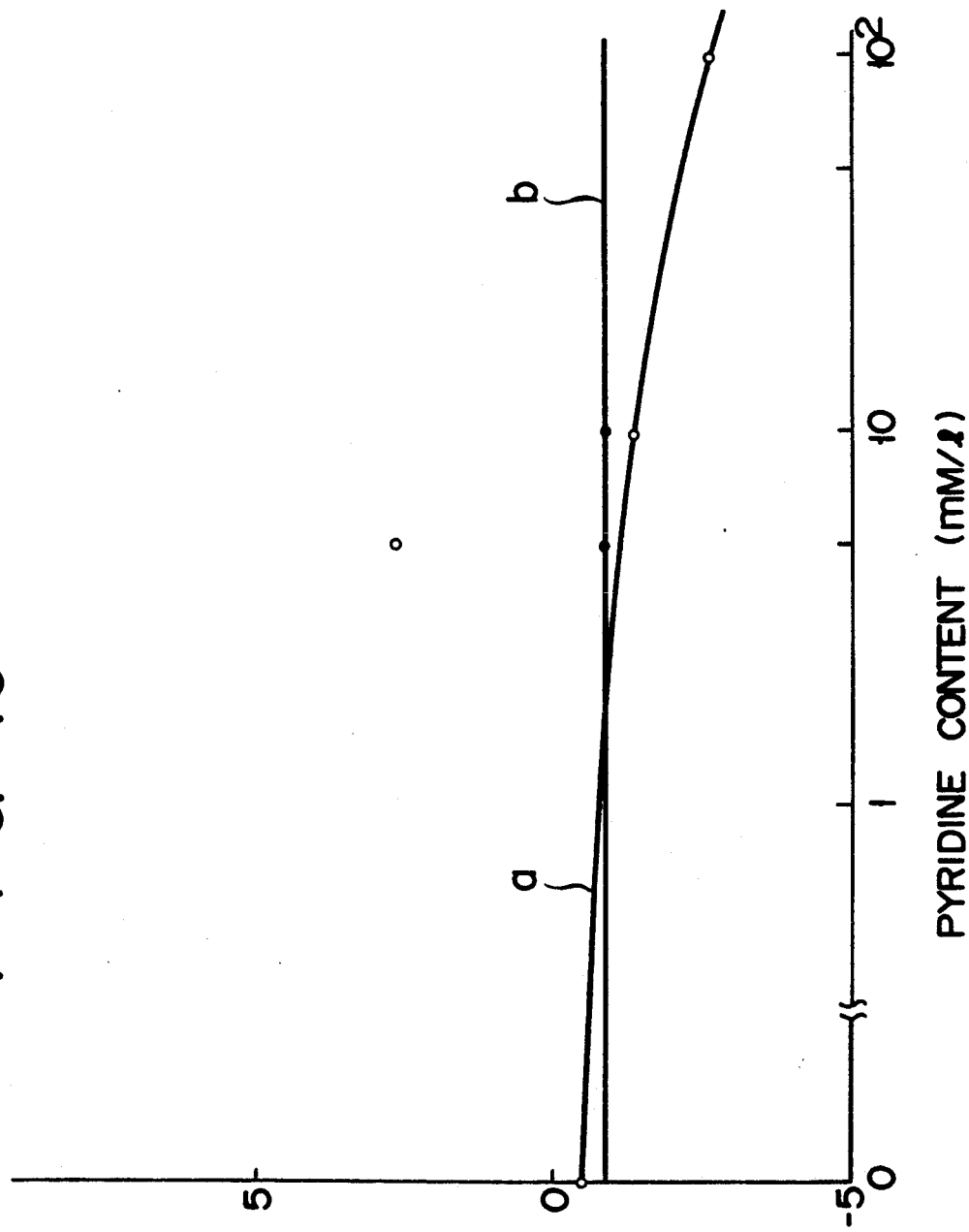

Both the influence of the oxygen partial pressure (pO$_2$) and of standard serum (Versatol) on the equilibrium potential was examined using the pH sensors prepared in Examples 13 to 32. Response times near a pH of 7.0 were also measured. The obtained results are shown in Table 5. FIGS. 9 and 10 show the relationship between the pyridine content in AP electrooxidation polymerization and the value ΔE (the E value at the saturated oxygen partial pressure minus the E value at the dissolved oxygen partial pressure under air (25° C.)). Referring to FIG. 9, hollow dots correspond to Test Examples 16 to 20, while solid dots correspond to Test Examples 21 to 25. Referring to FIG. 10, curve a corresponds to Test Examples 26 to 30, while curve b corresponds to Test Examples 31 to 35. As a result, the value ΔE is small and the equilibrium potential is stable in the order of TBABF$_4$-THF system, TBABF$_4$-CH$_3$CN system, NaClO$_4$-THF system, NaClO$_4$-CH$_3$CN system.

Figure 11:
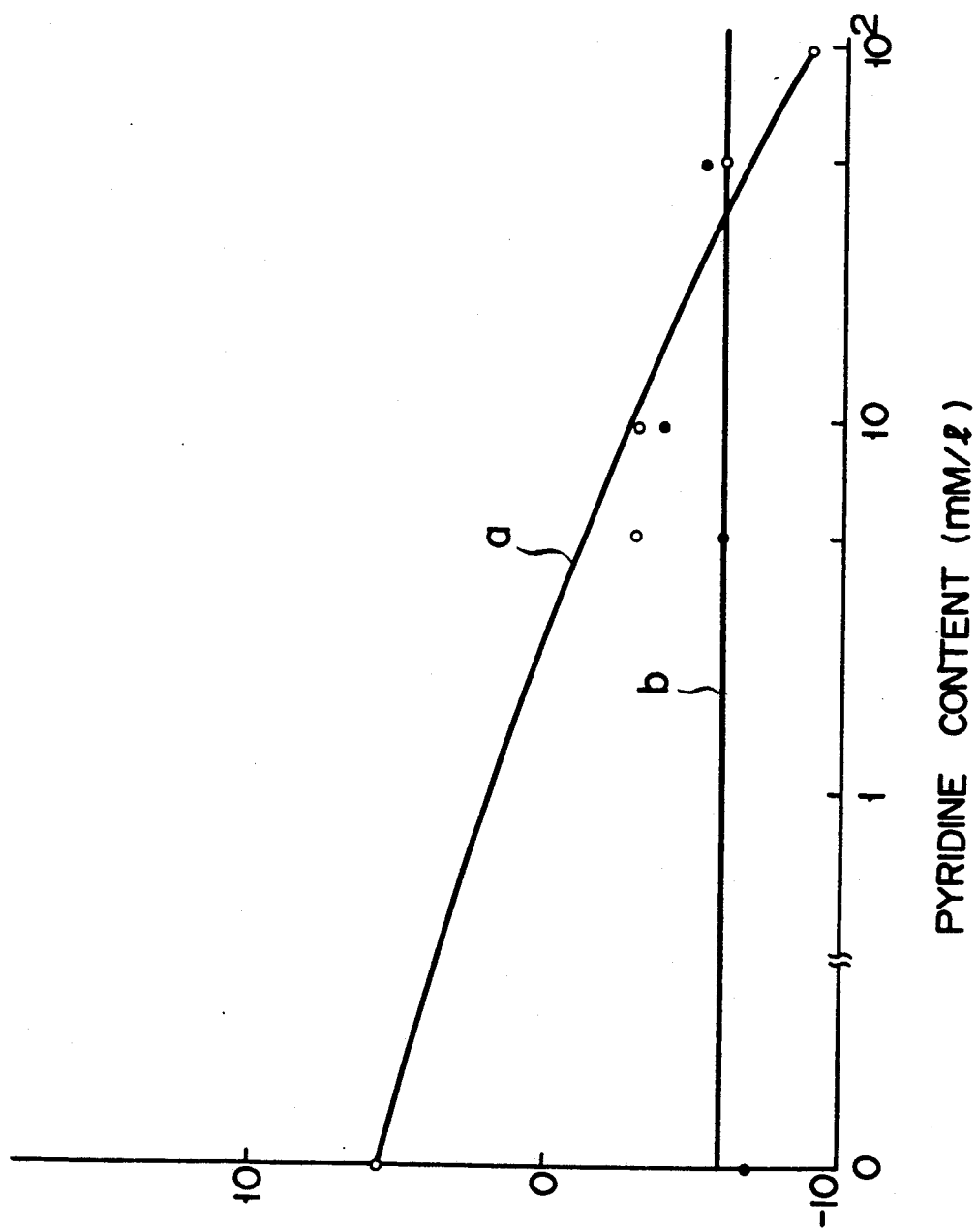
Figure 12:
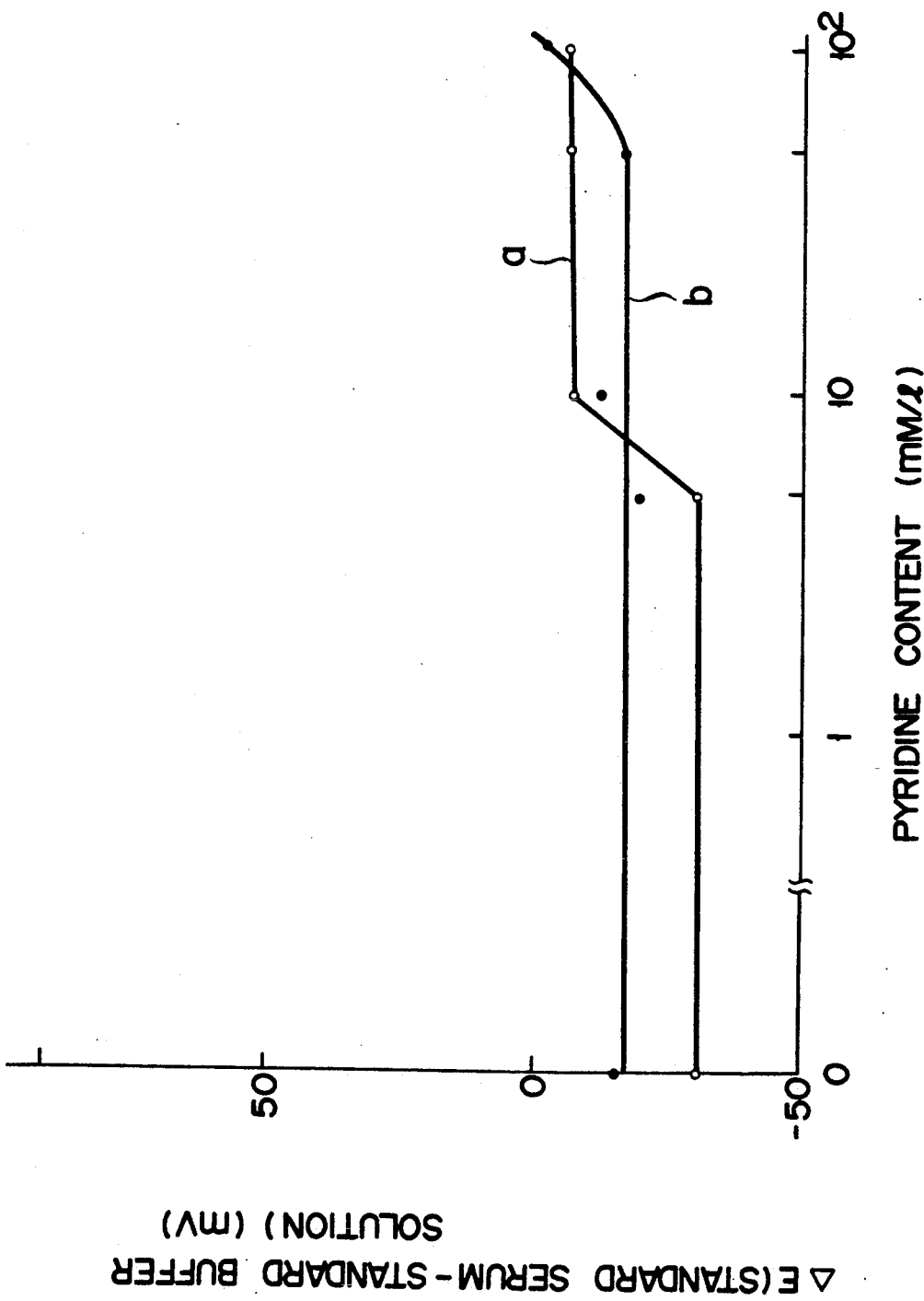

FIGS. 11 and 12 show the relationship between the pyridine content and the difference between the E value in standard serum and the E value in the standard solution (phosphate buffer solution). Referring to FIG. 11, curve a corresponds to Test Examples 16 to 20, and curve b corresponds to Test Examples 21 to 25. Referring to FIG. 12, curve a corresponds to Test Examples 26 to 30, and curve b corresponds to Test Examples 31 to 35. From the above results, it is seen that the above-mentioned difference is small in the order of NaClO$_4$-CH$_3$CN system, TBABF$_4$-CH$_3$CN system, TBABF$_4$-THF system, NaClO$_4$-THF system. It is also seen that when the supporting electrolyte is TBABF$_4$, the difference is not dependent on the pyridine content and is substantially constant. The response time is short in the order of NACIO$_4$-THF system, NaClO$_4$-CH$_3$CN system, TBABF$_4$-CH$_3$CN system, TBABF$_4$-THF system.

TABLE 5

| Test Example | pH Sensor Example No. | ΔE(mV) Po2 (mmHg) 736.2 − 147.0 | EO (Standard Phosphoric Acid Buffer Solution) - E (Standard Serum) (mV) | Response Time |
| --- | --- | --- | --- | --- |
| 16 | 13 | 1.5 | 5.5 | 1 min |
| 17 | 14 | 1.8 | −3.0 | 1 min |
| 18 | 15 | 0.3 | −3.0 | 6 sec |
| 19 | 16 | 0.7 | −6.0 | 6 sec |
| 20 | 17 | 11.4 | −9.0 | 36 sec |
| 21 | 18 | 0.6 | −7.0 | 7 sec |
| 22 | 19 | 0.6 | −6.0 | 1 min |
| 23 | 20 | 0.5 | −4.0 | 2.5 min |
| 24 | 21 | 0.7 | −5.5 | 30 sec |
| 25 | 22 | 3.1 | −10 | 1.0 min |
| 26 | 23 | 0.5 | −31.5 | 12 sec |
| 27 | 24 | 2.7 | −30.5 | 12 sec |
| 28 | 25 | −1.3 | −7.5 | 6 sec |
| 29 | 26 | −1.5 | −6.0 | 6 sec |
| 30 | 27 | −2.6 | −6.0 | 6 sec |
| 31 | 28 | −0.5 | −16 | 23 sec |
| 32 | 29 | −0.9 | −19 | 54 sec |
| 33 | 30 | −0.8 | −12 | 1 min |
| 34 | 31 | −0.4 | −16.5 | 3 min |
| 35 | 32 | −0.9 | −2.0 | 5 min |

EXAMPLES 33-37

The outer circumferential surfaces of disks of BPG as in Example 1 were insulated with thermally shrinkable tubes, mercury was filled in the tubes, and bases and lead wires were connected. Then, polymer films of 1-aminopyrene (AP) were formed on the surfaces of the BPG disks by electrooxidation polymerization.

ELECTROOXIDATION POLYMERIZATION

AP electrooxidation polymerization was performed in a three electrode cell using the partially insulated BPG disk as a working electrode, an SSCE as a reference electrode and a platinum net as a counter electrode. The electrolytic solution used was an acetonitrile solution containing 0.1M sodium perchlorate, 10 mM of AP and 10 mM of pyridine. Electrolysis was performed by constant potential electrolysis for 10 minutes at +1.0 V (with reference to the SSCE; this will be the same in the following description) after the potential of the working electrode was swept three times from 0 V to +1.0 V with reference to the SSCE. After the electrolysis, the working electrode was washed with water and dried. The film formed under these electrolysis conditions had a thickness of about 50 μm.

Each electrode obtained in this manner was immersed in an electrolytic solution shown in Table 6 for 48 hours, washed with water, dried and coated with a hydrogen ion carrier film as in Example 1. The film thickness was about 600 μm.

TABLE 6

| Example | Immersion Solution | Slope of Nernst Plot (mV/pH) | pH Region | 95% Response Time |
|---|---|---|---|---|
| 33 | Phosphate Buffer Solution (pH 6.86) | −58 | 4.0–9.2 | 1 min |
| 34 | 0.2M K$_2$HPO$_4$ | −58 | 4.0–9.2 | <30 sec |
| 35 | 0.2M NaClO$_4$ | −56 | 4.0–9.2 | <30 sec |
| 36 | 0.2M NaClO$_4$ + 5% HCHO | −61 | 4.0–9.2 | 1 min |
| 37 | 0.2M KCl | −30 | 4.0–9.2 | 5 min |

(25 ± 0.1° C.)

As can be seen from Table 6, the ion sensors having redox polymers impregnated with electrolytes had slopes of Nernst's plots of about −59 mV/pH except for Example 37 wherein KCl was used as an electrolyte, and also had good sensor characteristics including response time.

EXAMPLE 38

An electrode was prepared by forming a hydrogen ion carrier film of about 400 μm thickness following the same procedures as in Example 33 except that the solution used for forming the hydrogen ion carrier film had the following composition. The sensor characteristics of the resultant electrode were examined. The step response in solutions having different pHs and the difference of electrode potential between a standard phosphate buffer solution and a standard serum having the same pH were examined. The obtained results are shown in Table 7.

| | |
|---|---|
| TDDA | 1.0% by weight |
| KTpClPB | 0–0.614% by weight |
| Vinyl chloride (Pn 1,050) | 32.8% by weight |
| DOS | 65.6% by weight |
| THF | 10 ml |

TABLE 7

| | KTpClPB (% by weight) | Slope of Nernst plot (mV/pH) | Es*−Ep* (mV) | Step Response** | | | | |
|---|---|---|---|---|---|---|---|---|
| | | | | 7.46 ↓ 8.17 | 8.17 ↓ 7.46 | 7.46 ↓ 6.36 | 6.36 ↓ 5.36 | 5.36 ↓ 4.60 |
| 1 | 0 | −58 | −11 | 6 min | 11 min | 14 min | 29 min | — |
| 2 | 0.018 | −60 | +4.5 | 2 sec | <6 sec | <6 sec | 18 sec | 18 sec |
| 3 | 0.064 | −58 | +6.0 | 1 min | <6 sec | <6 sec | 13 sec | <6 sec |
| 4 | 0.18 | −2 | — | — | — | — | — | — |
| 5 | 0.614 | — | — | — | — | — | — | — |

(25 ± 0.1° C.)
*Es and Ep represent electrode potentials in standard serum and standard phosphate buffer solution, respectively.
**for example, represents a step response when a solution of pH 7.46 is replaced with a solution of pH 8.17. The step response is a 95% response time.

As can be seen from Table 7, the Nernst's plot had a slope of about −59 mV and the sensor characteristics were good within a KTpClPB concentration range of 0 to 0.064% by weight. However, when the KTpClPB concentration is 0, step response is slow. When the KTpClPB concentration exceeds 0.18% by weight, the Nernst's plot has a slope of almost 0 and the carrier substance does not exhibit its function, providing an impractical sensor. The difference (Es−Ep) slightly changed in accordance with change in the KTpClPB concentration.

EXAMPLE 39

An electrode was prepared by forming a hydrogen ion carrier film having a thickness of about 300 to 400 μm following the same procedures as in Example 38 except that the solution for forming the hydrogen ion carrier film had a composition as shown below. The sensor characteristics and so on of the resultant electrode were examined. The obtained results are shown in Table 8.

| | |
|---|---|
| TDDA | 0–9.2% by weight |
| KTpClPB | 0.6% by weight |
| Vinyl chloride (Pn 1,050) | 32% by weight |
| DOS | 65% by weight |
| THF | 10 ml |

TABLE 8

| | TDDA (% by weight) | Slope of Nernst plot (mV/pH) | Es*−Ep* (mV) | Step Response** | | | | |
|---|---|---|---|---|---|---|---|---|
| | | | | 7.48 ↓ 8.19 | 8.19 ↓ 7.48 | 7.48 ↓ 6.57 | 6.57 ↓ 5.34 | 5.34 ↓ 4.61 |
| 1 | 0 | — | — | — | — | — | — | — |
| 2 | 0.3 | −26 | +11.5 | 1.4 min | 24 min | 15 min | 11 min | 9 min |
| 3 | 1.0 | −54 | −4.5 | 4 min | <6 sec | 7 min | 3.5 min | 3 min |
| 4 | 2.9 | −59 | −3.5 | 4.5 min | <6 sec | 3.4 min | 6 min | 36 sec |
| 5 | 9.2 | −54 | −4.5 | 3.5 | 3.5 | 30 | 13 | 15 |

TABLE 8-continued

|  | Slope of Nernst plot (mV/pH) | Es*- Ep* (mV) | Step Response** | | | | |
|---|---|---|---|---|---|---|---|
| TDDA (% by weight) | | | 7.48 ↓ 8.19 min | 8.19 ↓ 7.48 min | 7.48 ↓ 6.57 sec | 6.57 ↓ 5.34 min | 5.34 ↓ 4.61 min |

*Same as in Table 7
**Same as in Table 7

As can be seen from Table 8, good characteristics were obtained when the TDDA content was 1.0% by weight or more. The difference (Es−Ep) was substantially constant within this TDDA content range.

EXAMPLE 40

A copper wire as a leading wire was adhered to one end face (surface area: $7.85 \times 10^{-3}$ cm$^2$) of a small piece (diameter: 1.1 mm; length: 5.0 mm) of basal plane pyrolytic graphite (BPG) as a conductive base using a conductive adhesive ("C-850-6" available from Amicon K.K.). The base was inserted into a teflon tube (inner diameter: 1.3 mm; length: 50 mm) such that the opposite surface of the base not having the leading wire adhered projected from the end face of the teflon tube. After filling an insulating adhesive in a gap between the teflon tube and the base, the projecting distal end face of the base was cleaved into a thin film to expose a new surface.

Electrooxidation polymerization was performed in a three electrode cell under the following conditions using the base prepared in this manner as a working electrode, a saturated sodium chloride calomel electrode (SSCE) as a reference electrode, and a platinum mesh as a counter electrode. An electrooxidation polymer film was formed on an exposed surface of the base.

An electrolytic solution used was obtained by adding 10 mM/l of 1-aminopyrene and 10 mM/l of pyridine to an acetonitrile solvent containing 0.1 M/l of sodium perchlorate as a supporting electrolyte. After the working electrode potential was swept three times at a sweeping speed of 50 mV/sec within a potential range of 0 to +1.0 V (with reference to the SSCE), constant potential electrolysis was performed at +1.0 V for 10 minutes. In this manner, an electrooxidation polymerization film of 1-aminopyrene (oxidation/reduction film) was formed on the exposed surface of the base. After the base was rinsed well, it was stored in a phosphate buffer solution having a pH of 6.86 for one day so as to stabilize the oxidation/reduction potential of the oxidation/reduction film. After the base was dried, a hydrogen ion carrier film was formed in the following manner.

25.6 mg of tri-n-dodecylamine, 5.7 mg of potassium-tetrakis(p-chlorophenyl) borate, 732 mg of dioctyl sebacate and 367 mg of vinyl chloride (average polymerization degree: 1,050) were dissolved in 10 ml of tetrahydrofuran. 2 µl of the resultant solution were coated and dried three times on the surface of the oxidation/reduction film. The obtained structure was inserted in a heat shrinkable tube such that the distal end of the tube extended outward from the end face of the base by 1 mm. A polyvinyl chloride paste of the following composition was filled in the gap, and a heat treatment was performed at 140° C. for about 5 minutes to solidify the resin.

| Composition of Polyvinyl Chloride Paste | |
|---|---|
| Tri-n-dodecylamine | 25.6 mg |
| Potassiumtetrakis(p-chlorophenyl) borate | 5.7 mg |
| Dioctyl sebacate | 732 mg |
| Polyvinyl chloride paste resin (polymerization degree: 1,000) | 367 mg |

The solution was filled in the gap after deaeration at a reduced pressure of $10^{-1}$ to $10^{-2}$ mmHg for about 10 hours.

The pH sensor of the present invention was prepared in this manner. Total thickness of oxidation/reduction film and hydrogen ion carrier film was 1 mm.

TEST EXAMPLE 36

The relationship between the equilibrium potential of the pH sensor prepared in Example 40 and the pH measuring by glass pH electrode in the solution was examined. More specifically, a SSCE was used as a reference electrode, a standard phosphate buffer solution was used as this measuring solution, and the pH of this solution was changed in the order of 6.55, 7.48 and 8.12 (the pH was measured with a glass electrode in advance). The measurement temperature was kept constant at 38.5° C. The obtained results are shown in FIG. 13.

Figure 13:
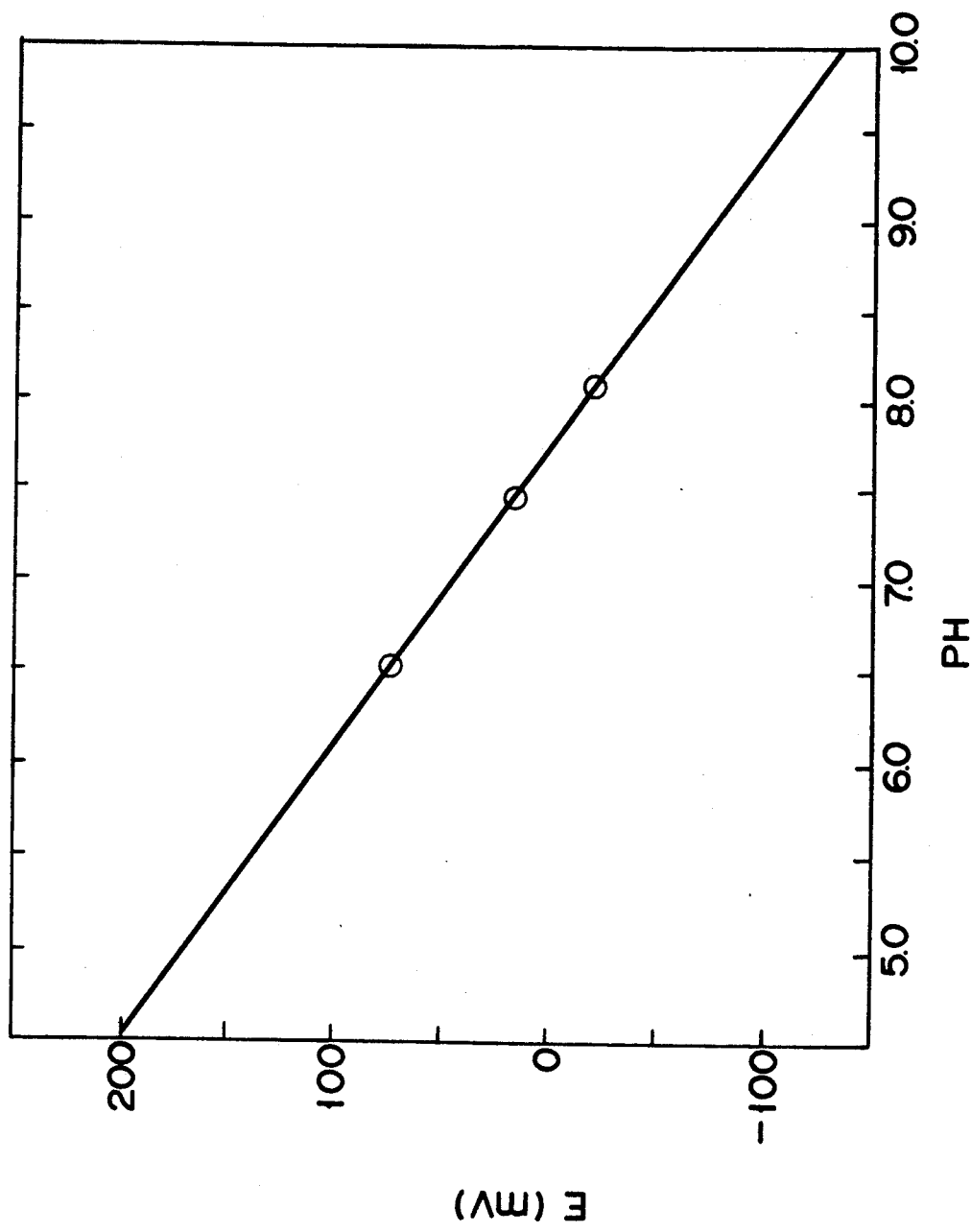

The linear relationship between the equilibrium potential and the pH value shown in FIG. 13 satisfies the following Nernst equation:

$$E = E_0 - (RT/F) \ln [H^+] \tag{1}$$

(where
E is the equilibrium potential (with reference to SSCE) of the pH sensor;
$E_0$ is standard electrode potential;
R is the gas constant;
T is the thermodynamic temperature (K);
F is the Faraday constant; and
$-\ln [H^+]$ is the pH)

In this Test Example, $E_0$ was 482.0 mV and the value corresponding to (RT/F) was 61.4 mV (38.5° C.).

The pH can be calculated by the following equation (2) in accordance with the equilibrium potential E of the pH sensor:

$$pH = -\ln [H^+] = -(E - 482.0)/61.4 \tag{2}$$

In this test, the time required for the pH sensor to reach 95% of the equilibrium potential (95% response time) was about 6 to 30 seconds, demonstrating a very rapid response.

TEST EXAMPLE 37

Using the pH sensor and the reference electrode used in Test Example 36, the blood pH of the dog (mixed breed; weight: 25 kg) was continuously measured in an extracorporeal blood circuit outside the body of the dog for 17 hours. As shown in FIG. 26, blood sampled from the carotid (artery) of a dog 41 was circulated through a polyvinyl chloride tube 42 (inner diameter: 8.0 mm) via a flow meter 43, a roller pump 44, a heat exchanger 45 and hollow fiber-type oxygenator 46 (four units each having a total membrane area of 0.5 m², corresponding to an oxygen gas flow rate of 0.5 l/min), and oxygenized blood was returned to the artery of the dog. The blood flow rate (flow direction is indicated by arrows) was 1.2 l/min, and the extracorporeal blood temperature was kept at 38.5° C. by the heat-exchanger 45. A pH sensor 10 (one prepared in Example 40) of the present invention, a reference electrode (SSCE) 53 and a temperature sensor 47 were inserted into the tube 42 at the carotid artery side such that each extended at its distal end into the tube 42 by about 1 mm. The pH sensor 10 and the reference electrode 53 were connected to a potentiometer 54. The potentiometer 54 and the temperature sensor 47 were connected to a computer 49 ("FM-11" available from FUJITSU) through a GP-IB interface adapter 48. The computer 49 was used to calculate the pH in accordance with equation (2) above. The calculated result was displayed on a display device 50.

For reference, the pH of blood was measured together with the blood carbon dioxide gas partial pressure and the oxygen gas partial pressure by a blood gas meter "BMS-MK-2" available from Radiometer Inc. (capable of measuring the blood gases and pH). Since the blood gas meter could only measure the pH at 37° C., the measured pH was corrected by the following equation (3):

$$pH = pHm + [-1.46 \times 10^{-2} + 6.5 \times 10^{-3}(7.4 - pHm)](t - 37) \quad (3)$$

(wherein pHm is the pH (37° C.) measured by the blood gas meter described above, and t is the temperature of the dog blood (38.5° C.), to obtain a pH at 38.5° C.

The obtained results are shown in Table 9 below.

TABLE 9

| Measurement Time (Hour) | pH Sensor of Present Invention (38.5° C.) | pH Blood Gas Meter* Corrected Value | pH Blood Gas Meter* Actual Measurement (37° C.) | Blood Gas Partial Pressure (mmHg) CO₂ | Blood Gas Partial Pressure (mmHg) O₂ |
|---|---|---|---|---|---|
| 0 | 7.40 | 7.40 | 7.422 | 19.8 | 339 |
| 40 min | 7.40 | 7.38 | 7.401 | 22.5 | 301 |
| 2 | 7.44 | 7.42 | 7.416 | 22.7 | 273.5 |
| 6 | 7.47 | 7.46 | 7.486 | — | — |
| 8 hour 30 min | 7.52 | 7.53 | 7.536 | 17.3 | 270 |
| 11 hour 40 min | 7.54 | 7.54 | 7.548 | 17.2 | 216 |
| 15 | 7.47 | 7.45 | 7.470 | 22.1 | 152 |
| 17 | 7.40 | 7.43 | 7.450 | 23.0 | 154 |

Note: Measurements in columns marked with "*" were obtained with a "BMS-Mk-2[ gas meter available from Radiometer Inc.

It is seen from the above results that the blood pH can be quickly and correctly measured using a pH sensor of the present invention. Since plasma leakage (a phenomenon occurring when an artificial lung is used) occurred, various pH adjusting agents ("Mioblock" an anesthetic muscle relaxant) available from Sankyo Seiyaku K.K.; "Meiron" (sodium hydrogen carbonate) available from Otsuka Seiyaku K.K., and "Hespander" (artificial plasma available from Kyorin Seiyaku K.K.) were added at predetermined intervals. It was confirmed with the pH sensor of the present invention that the pH of the blood shifted to the alkaline side within several seconds upon administration of the respective pH adjusting agents, thereby demonstrating excellent response characteristics of the pH sensor of the present invention.

EXAMPLE 41

A pH sensor of the shape as shown in FIG. 2 was prepared by the following method.

A column having a diameter of 1.3 mm was cut off from a plate of basal plane pyrolytic graphite (BPG) (available from Union Carbide Corp.) A leading wire 27 was connected to a bottom surface 21b of the column with a conductive adhesive 25 ("C-850-6" available from Amicon K.K.) The structure was inserted into a teflon tube 22a having a diameter of 1.7 mm, and an insulating material 22b ("TB2067" available from Three Bond Inc.) was filled for electrical insulation. A distal end 21a of an electrode of the thus obtained BPG base 21 was cleaved by a knife blade to expose a new surface. Using this as a working electrode, a saturated sodium chloride calomel electrode (SSCE) as a reference electrode and a platinum mesh as a counter electrode, electrooxidation polymerization was performed under the following conditions to form an oxidation/reduction polymer film 23 on the surface of the base distal end face 21a.

The electrolytic solution was an acetonitrile solution which contained 0.2M/l of sodium perchlorate as a supporting electrolyte and 0.5M/l of 2,6-dimethylphenol (2,6-xylenol) as a monomer. Electrooxidation polymerization was performed by sweeping the electrolysis voltage within a range of 0 V to 1.5 V (with reference to the SSCE) at a sweeping speed of 50 mV/sec three times, and then performing constant potential electrolysis at 1.5 V for 10 minutes.

A film formed in this manner (dark blue in a dry state) was washed with methanol (the film color changed to orange), and was thereafter dipped in a phosphate buffer solution having a pH of 7.4 so as to stabilize the potential of the oxidation/reduction film.

After the oxidation/reduction film electrode was rinsed with water, it was dried and a hydrogen ion carrier film was formed thereover in the following manner.

A coating solution A was prepared by dissolving in 10 ml of tetrahydrofuran (THF) 25.6 mg of tri-n-dodecylamine (TDDA) as a hydrogen ion carrier, 5.7 mg of potassiumtetrakis(p-chlorophenyl) borate (KTpClPB) as an electrolyte salt, 367 mg of polyvinyl chloride ("PSL-10" (PVC) available from Kanegafuchi Chemical Industry Inc.; average polymerization degree: 1,000) as a polymer, and 732 mg of dioctyl sebacate (DOS). The coating solution A was coated on the surface of the oxidation/reduction film in an amount of 2 μl so as to reinforce the oxidation/reduction film. The electrode was inserted into a PVC tube 26. After filling a paste resin solution of the following composition, the structure was heated at 140° C. for 1 minute to gelate the resin and to form a hydrogen ion carrier film 24 of about 1 mm thickness. In order to close a gap due to a volume reduction upon gelation, the coating solution A was coated and dried several times and the electrode was subjected to the following Test Example.

| Paste Resin Composition | |
|---|---|
| TDDA | 0.3 g |
| KTpClPB | 0.18 g |
| DOS | 19.68 g |
| PVC | 9.84 g |

TEST EXAMPLE 38

Figure 14:
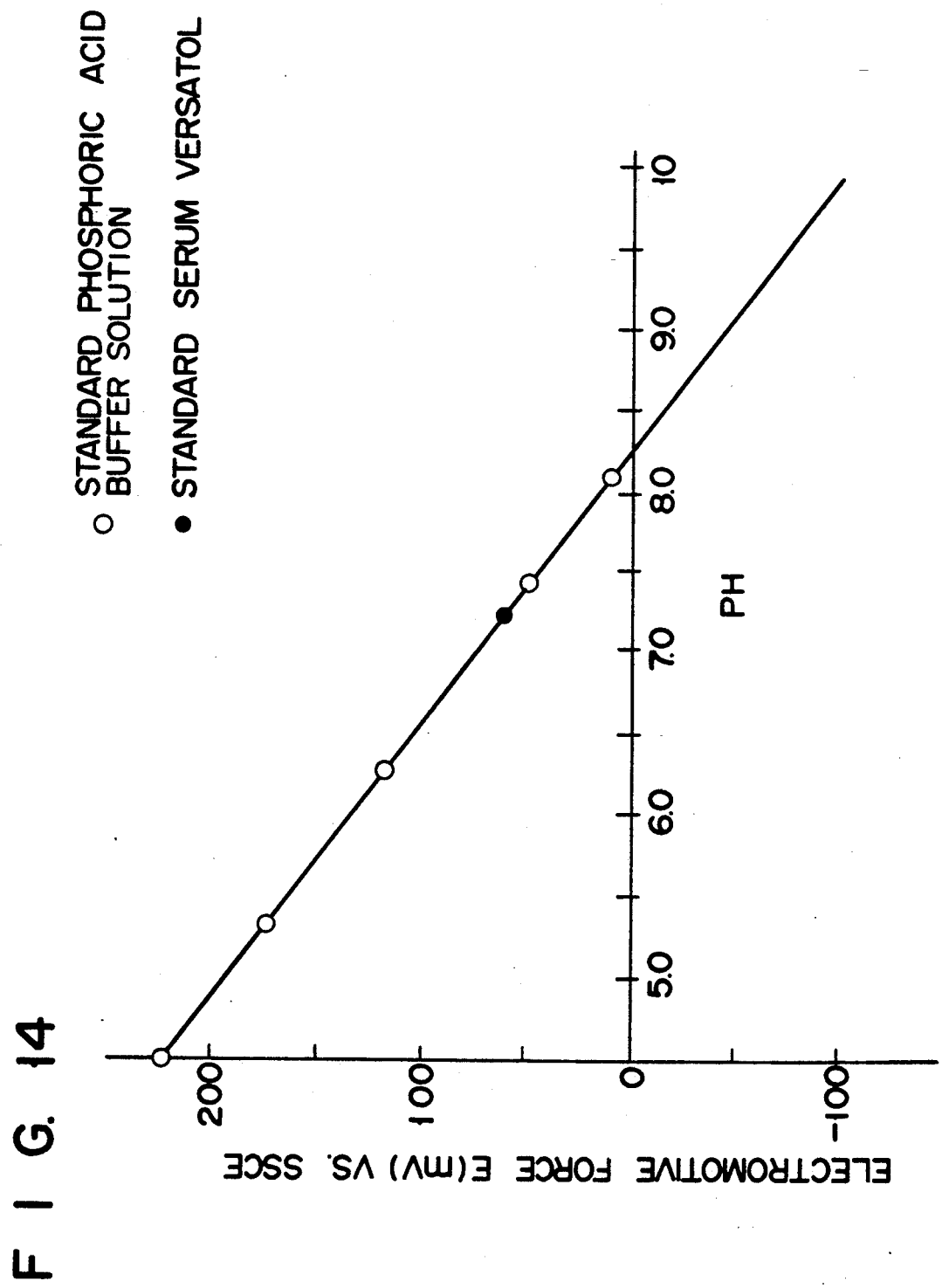

The electromotive force of the pH sensor prepared in Example 41 in standard phosphate buffer solutions (pH: 4.54, 5.32, 6.47, 7.45, and 8.10) were measured with a two electrode cell. The reference electrode used was a saturated sodium chloride calomel electrode (SSCE) and measurement was performed at 37° C.±0.1° C. The obtained results are shown in FIG. 14. FIG. 14 also shows the measured pH of standard serum ("Versatol A" available from Warner Lambert Inc.) in place of the standard phosphate acid buffer solution.

As can be seen from FIG. 14, the electromotive force E and the pH have an excellent linear relationship and the line has a slope of −60 mV/pH. This value of the slope roughly coincides with the value (−61.2 mV/pH) calculated in accordance with the Nernt equation.

The electromotive force of the same sensor was similarly measured 9 days after, 15 days after and 27 days after the manufacture of the sensor so as to examine stability of the Nernst's plot over time. The obtained results are shown in FIGS. 15 and 16.

Figure 15:
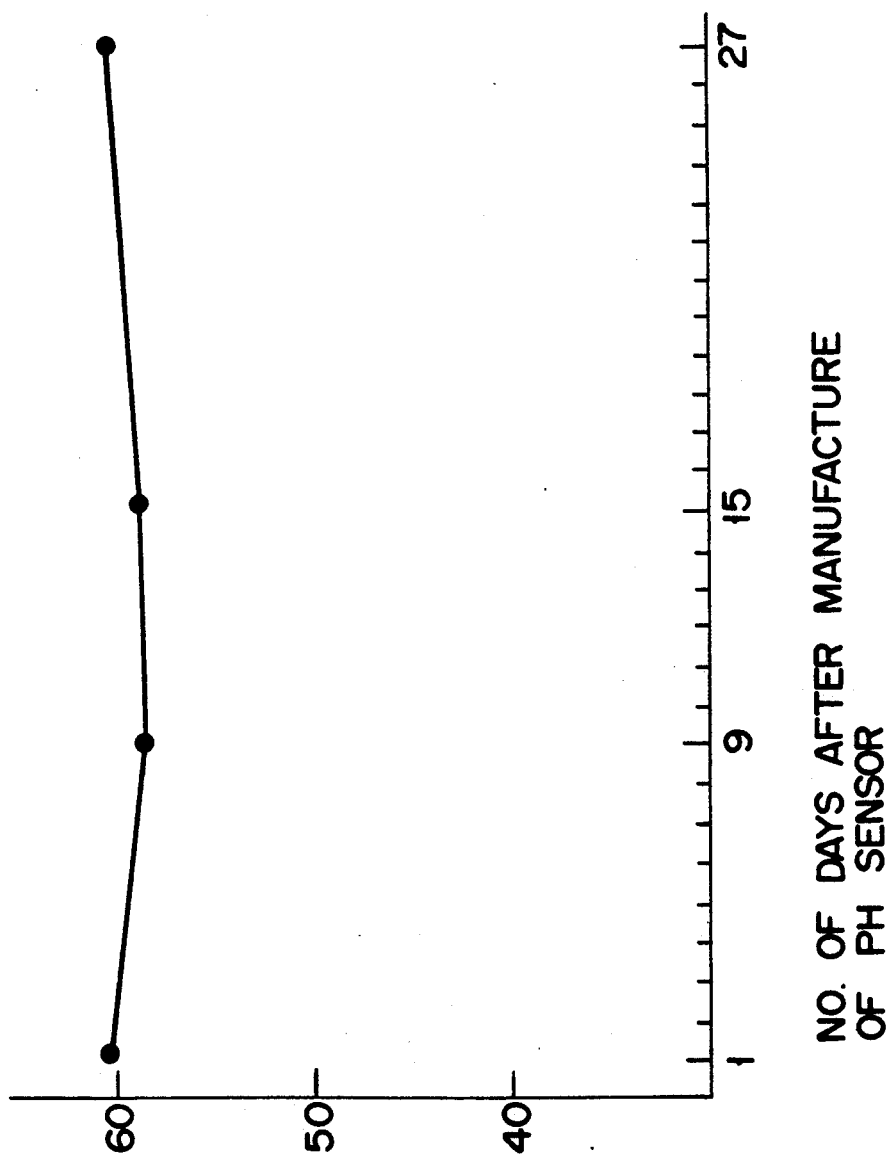
Figure 16:
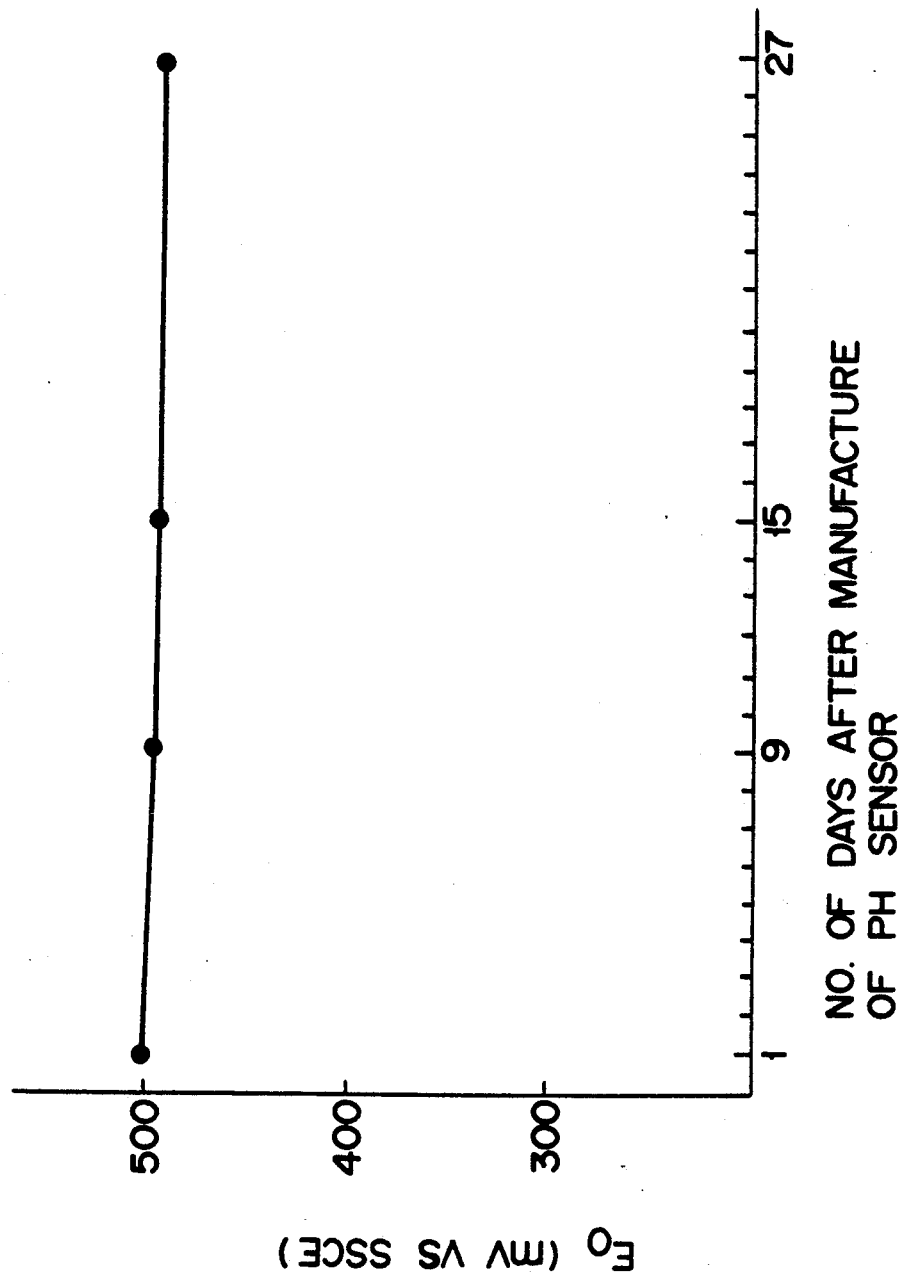

As can be seen from FIGS. 15 and 16, within about 10 days from the manufacture of the sensor, the slope of the Nernt's plot becomes an ideal value of −60 mV/pH and the value $E_0$ also converges to 500 mV with reference to the SSCE. Therefore, a Nernt's plot obtained 10 days or longer after manufacture of the sensor can be used as a calibration curve.

The pH response time of the pH sensor prepared in Example 41 was within 5 seconds (95% response time), a much shorter period than usual.

TEST EXAMPLE 39

Figure 17:
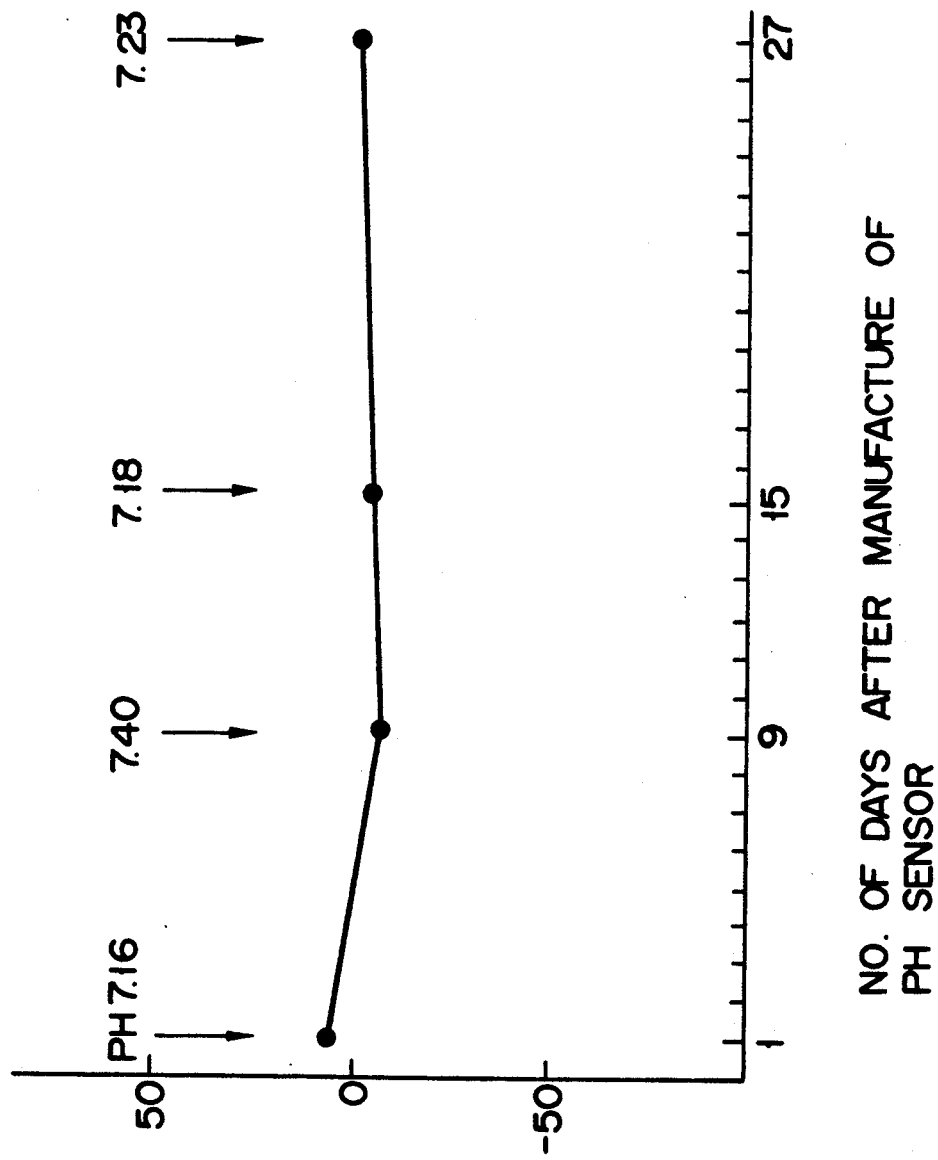

The electromotive force $E_1$ in a standard serum Versatol (available from Warner Lambert Inc.) solution was measured by the pH sensor prepared in Example 41. The pH of the solution was measured by a commercially available glass electrode ("91-02" available from Orion Inc.) The electromotive force $E_2$ to be indicated by the electrode of the present invention at this pH value was calculated from the calibration curve (FIG. 14) and was compared with $E_1$. The differences in electromotive force generated by the electrodes ($\Delta E = E_1 - E_2$) were plotted as a function of the number of days after the manufacture of the pH sensors, and the obtained results are shown in FIG. 17. The calibration curve obtained with Test Example 1 was used in pH measurement by the pH sensors.

As can be seen from FIG. 17, substantially no difference was present in the pH value measured on the 10th day from the date of manufacture of the pH sensor, and thus the sensor of the present invention has a satisfactory precision after the operation is stabilized. When pH measurement by the sensor of the present invention was continued further, no variation was present in the pH measurements even after 2 to 3 months. The sensor of the present invention thus has an excellent durability.

When pH measurement was performed while changing the oxygen partial pressure $PO_2$ in standard serum within a range of 0 to 740 mmHg, the electromotive force was constant within an error of ±1 mV. This reveals that the sensor of the present invention is not affected by dissolved oxygen in a sample.

EXAMPLES 42-45

The outer circumferential surface of a disc base (diameter: 5 mm; thickness: 5 mm) of basal plane pyrolytic graphite (BPG) was covered and insulated with a heat shrinkable tube, mercury was filled in the tube, and a leading wire was connected to the base. Electrooxidation polymerization was performed under the following conditions in a three electrode electrolysis cell using the above structure as a working electrode, a saturated sodium chloride calomel electrode (SSCE) as a reference electrode, and a platinum mesh as a counter electrode. An electrooxidation polymer film was thus formed on the exposed surface of the base.

The electrolytic solution was obtained by adding 10 mM/l of 1-aminopyrene (AP) and 10 mM/l of pyridine to an acetone solvent containing 0.1 M/l of sodium perchlorate as a supporting electrolyte. After sweeping the potential of the working electrode at a sweeping speed of 50 mV/sec within a voltage range of 0 V to +1.0 V (with reference to the SSCE) three times, constant potential electrolysis was performed at +1.0 V (with reference to the SSCE) for 10 minutes. Thus, an electrooxidation polymer film (oxidation/reduction film) of 1-aminopyrene was formed on the surface of the base. The film was rinsed with water and immersed in a phosphate buffer solution having a pH of 6.86 for 30 minutes or more so as to stabilize the film. After the film was dried, a hydrogen ion carrier film was formed by the following method.

A solution was prepared by dissolving in 10 ml of tetrahydrofuran, prescribed amounts (Table 10) of tri-n-dodecylamine (TDDA), potassiumtetrakis(p-chlorophenyl) borate (KTpClTB), dioctyl sebacate (DOS), and polyvinyl chloride (PVC; average molecular weight ($\overline{P}n$): 1,050 and 2,500). The base having the oxidation/reduction film thereon was dipped in the solution and the solvent was dried so as to form a hydrogen ion carrier film on the oxidation/reduction film. A pH sensor of the present invention was thus prepared.

The pH sensor thus obtained was tested for its electrode resistance (to be referred to as film resistance hereinafter) mainly attributable to conductivity of the hydrogen ion carrier film and for its change in equilibrium potential (mV/pH) per pH at 25° C. The sample solution used was a 50 mM/l phosphate buffer solution. The obtained results are shown in Table 10.

TABLE 10

| Example No. | Hydrogen Ion Carrier Film Thickness (μm) | KTpClPB Content (g) | (% by wt) | PVC $\overline{Pn}$ | Content (% by wt) | DOS Content (% by wt) | TDDA Content (% by wt) | Hydrogen Ion Carrier Film Resistance** | mV/pH |
|---|---|---|---|---|---|---|---|---|---|
| 42 | 425 | 0 | 0 | 1,010 | 32.8 | 65.6 | 1.0 | 3.0 MΩ | 67 |
| 43 | 431 | 0.0409 | 0.6 | 2,500 | 32.8 | 65.6 | 1.0 | 750 KΩ | 65 |
| 44 | 418 | 0.0409 | 0.6 | 2,500 | 31.1 | 62.2 | 0.95 | 750 KΩ | 65 |
| 45 | 331 | 0.3442 | 5.7 | 2,500 | 32.8 | 65.6 | 1.0 | 500 KΩ | 5 |

*After 3 μl of 0.1% by weight solution of AP in acetonitrile were coated on the exposed end face of the substrate and dried, electrolysis (sweeping within a voltage range of −0.2 V to +0.6 V (with reference to the SSCE) for 5 minutes) was performed. A hydrogen ion carrier film was coated thereafter.
**The sample solution was 50 mM/l of a phosphate buffer solution (pH 7.44).

In order to calculate the internal resistance of the pH electrode, a circuit as shown in FIG. 27 was prepared, and calculation was performed in accordance with the following equation:

$$E = Vs(1 + Rx/Rs)$$

(where Rs is the standard resistance, Rx is the film resistance (internal electrode resistance), E is an applied voltage, and Vs is the voltage drop across Rs).

As can be seen from Table 10, the film resistance of the pH sensor changes in accordance with the content of KTpClPB. Also, a change in equilibrium potential (mV/pH) per pH decreases with an increase in the content of KTpClPB. When a hydrogen ion carrier film is not formed, the film resistance is 3.0 MΩ (0.196 cm² (base surface area)).

EXAMPLES 46-61 pH sensors having hydrogen ion carrier films of thicknesses as shown in Table 11 were prepared following the same procedures as in Example 41. The film resistances, response times, and changes in equilibrium potentials per pH of these pH sensors were measured following the same procedures as in Examples 42 to 45. The influence of the surface area of the BPG base was also considered. The obtained results are also shown in Table 11.

TABLE 11

| Example No. | Base Surface Area (cm²) | Hydrogen Ion Carrier Film Thickness (μm) | Hydrogen Ion Carrier Film Resistance** (mΩ) | Response Time (sec) | mV/pH |
|---|---|---|---|---|---|
| 46 | 5.0 × 10⁻³ | 0 | — | 6 to 22 (min) | 43 |
| 47 | 5.0 × 10⁻³ | 130 | 18 | <6 | 54 |
| 48 | 5.0 × 10⁻³ | 245 | 18 | <6 | 56 |
| 49 | 5.0 × 10⁻³ | 365 | 55 | 6 to 420 | 58 |
| 50 | 1.43 × 10⁻² | 0 | 2.25 | 9 to 28.5 (min) | 49 |
| 51 | 1.43 × 10⁻² | 75 | 3.5 | <6 | 51 |
| 52 | 1.43 × 10⁻² | 160 | 7 | <6 | 56 |
| 53 | 1.43 × 10⁻² | 195 | 8.5 | <6 | 56 |
| 54 | 0.196 | 0 | 0.5 | 5 (min) | 48 |
| 55 | 0.196 | 90 | 0.5 | <6 | 54 |
| 56 | 0.196 | 122 | 0.5 | <6 | 54 |
| 57 | 0.196 | 380 | 0.75 | <6 | 56 |
| 58 | 0.196 | 425 | 0.5 | <6 | 57 |
| 59 | 0.196 | 650 | 1 | <6 | 57 |
| 60 | 0.196 | 0,015 | 1.25 | <6 | 59 |
| 61 | 0.196 | 1,120 | 1.25 | <6 | 58 |

**Sample solution was 50 M/l phosphate buffer solution (pH 7.44).

Figure 18:
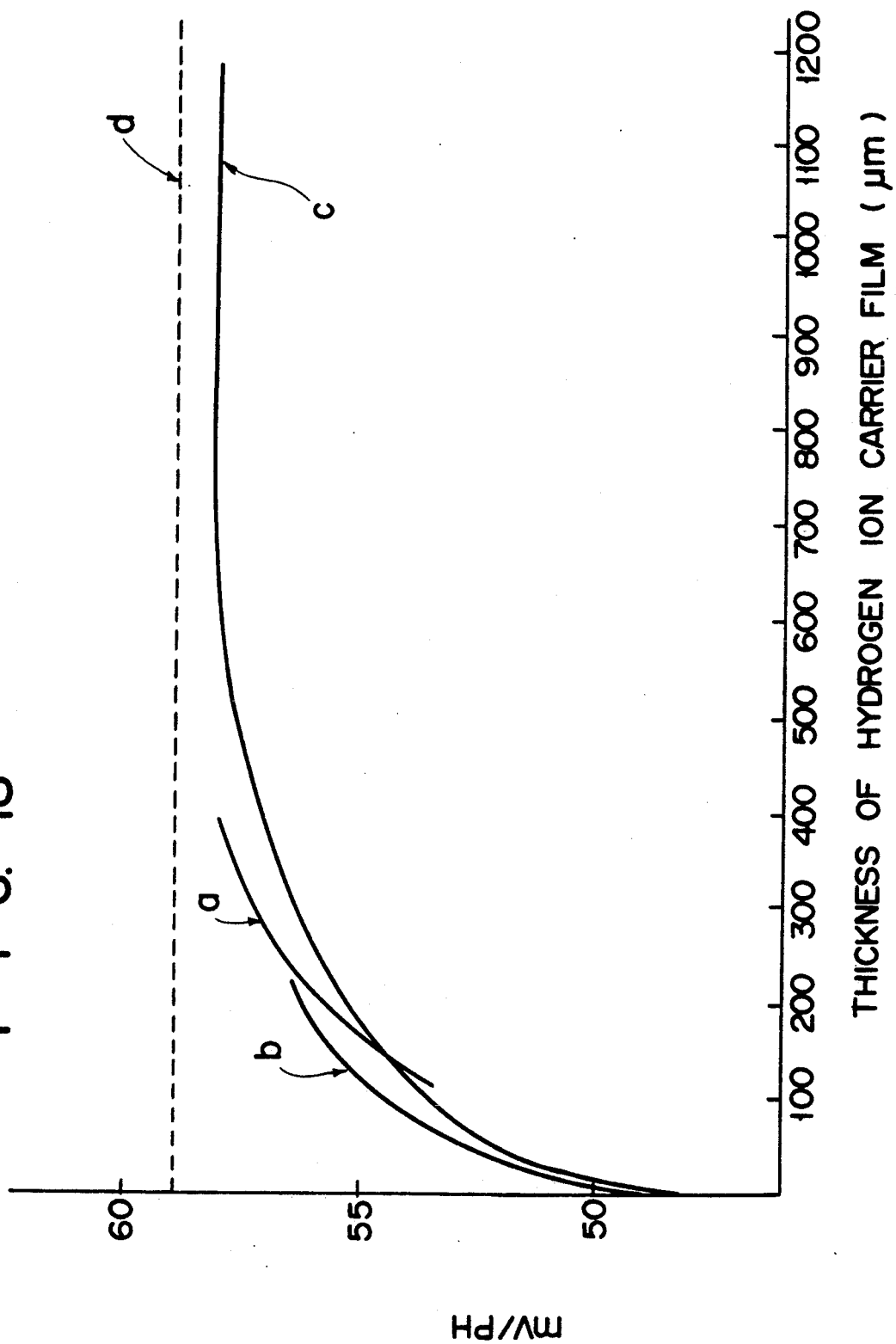

As can be seen from Table 11, the change in equilibrium potential per pH increases with an increase in thickness of the hydrogen ion carrier film for each case wherein the surface area of the BPG base was 5×10⁻³ cm² (Examples 46 to 49), 1.43×10⁻² cm² (Examples 50 to 53) and 0.196 cm² (Examples 54 to 61). These results are shown in FIG. 18. In FIG. 18, solid curve a corresponds to Examples 46-49, solid curve b corresponds to Examples 50 to 53, and solid curve c corresponds to Examples 54 to 61. In the case of Examples 54 to 61 (solid curve c), when the film thickness increases, a change in equilibrium potential per pH approximates to a theoretical pH response change 59.16 mV/pH (25° C.) according to the Nernst equation.

Figure 19:
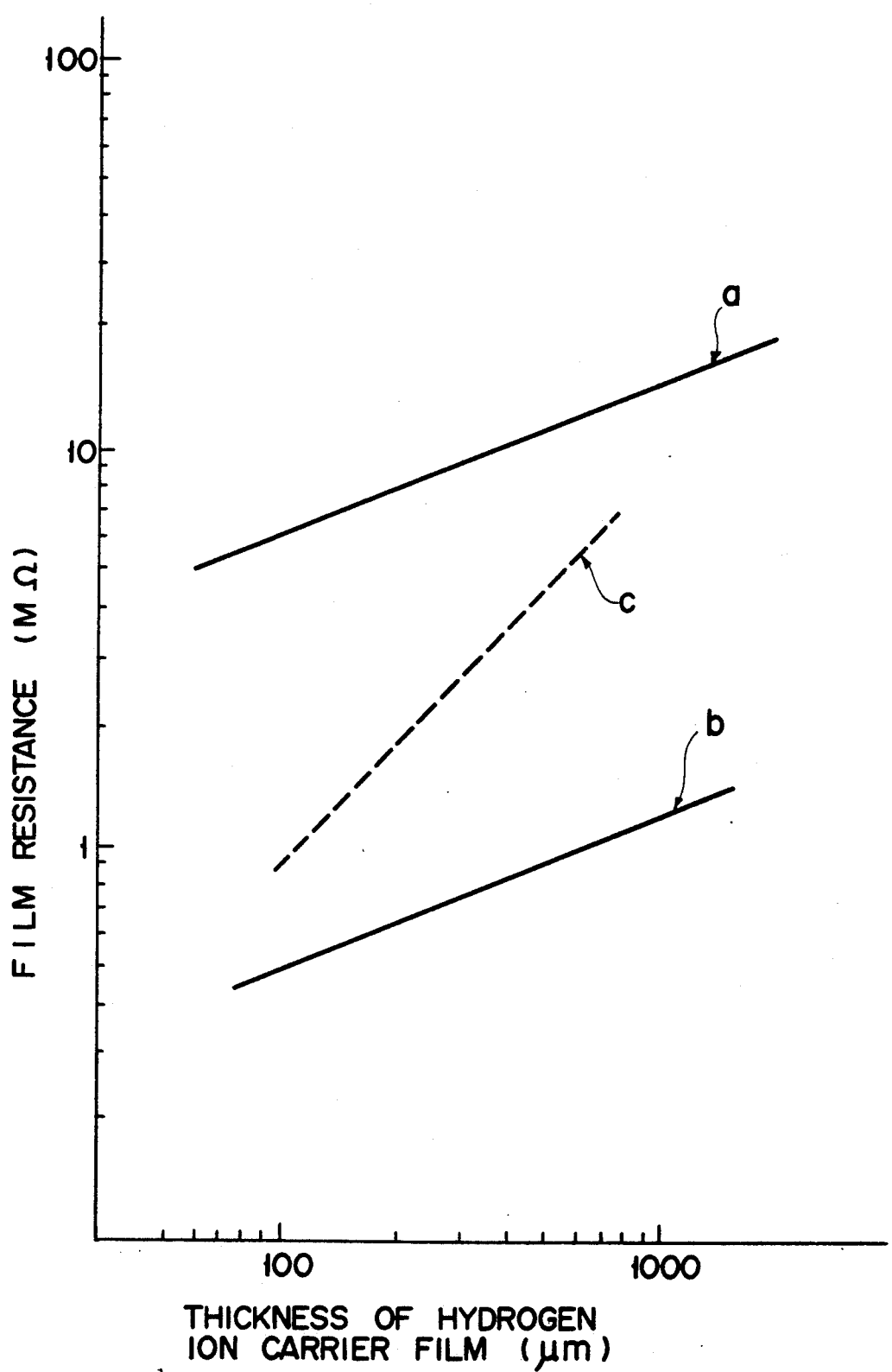

The relationship between the BPG base surface area and the film resistance as obtained from the results shown in Table 11 can be shown as in FIG. 19. Referring to FIG. 19, solid curve a corresponds to the sensors of Examples 50 to 53, while solid curve b corresponds to the sensors of Examples 54 to 61. Theoretically, when the logarithmic value of the film resistance is plotted as a function of the logarithmic value of the film thickness, a line having a slope of 1 (dotted line c) is obtained. However, with the electrode of the present invention, a slope of about 0.4 is obtained. This reveals that when a hydrogen ion carrier film is formed, an increase in film resistance with an increase in film thickness is suppressed.

As can be seen from FIGS. 18 and 19, when the film thickness is up to about 10 mm, the film resistance presents no practical problem. However, a satisfactory effect of forming a hydrogen ion carrier film can be obtained with a film thickness of about 3 mm.

In the pH sensors of almost all Examples, the response time is less than 1 minute and, particularly, less than 6 seconds, which is very fast.

It can be seen from this that the pH sensor can have optimum characteristics (change in equilibrium potential, response time and film resistance) when the hydrogen ion carrier film has a thickness of about 600 μm to 1 m.

EXAMPLE 62

A disk having a diameter of 5 mm was cut from a basal plane pyrolytic graphite (BPG) plate (available from Union Carbide Corp.) A leading wire was connected to the bottom of the disk with a conductive adhesive (available from Amicon K.K.). The disk was covered with a heat shrinkable tube such that the top of the BPG slightly projected from the insulating tube. The projecting distal end face of the BPG base was cleaved with a knife blade to expose a new surface. Electro-oxidation polymerization was performed using this structure as a working electrode, a saturated sodium chloride calomel electrode (SSCE) as a reference electrode and a platinum mesh as a counter electrode under the following conditions:

Electrolytic solution

Acetonitrile containing 0.2 M/l of sodium perchlorate as a supporting electrolyte and 0.5 M/l of 2,6-xylenol as a reactive substance Electrolysis condition After the electrolysis potential was swept three times (sweep rate of 50 mV/sec) within a range of 0 V to 1.5 V vs. SSCE, constant potential electrolysis was performed at 1.5 V for 10 minutes.

Thus, an electrooxidation polymer film (30 μm thickness) of 2,6-xylenol was formed on the exposed distal end face of the BPG base. The polymer film was dark blue in color. After the film was rinsed with water, it was dipped in a 0.01 M/l potassium chloride aqueous solution for 1 hour to stabilize the electrode potential. After rinsing with water, the film was dipped in an immersion solution having the following composition and dried so as to form a potassium ion carrier film on the oxidation/reduction film:

| | |
|---|---|
| Valinomycin | 1.6 mg |
| Polyvinyl chloride (Polymerization degree: 1,050) | 39.3 mg |
| Dioctyl sebacate (plasticizer) | 74.6 ml |
| Tetrahydrofuran | 5 ml |

The dipping/drying process was performed 20 times, and a potassium ion carrier film having a thickness of about 0.2 mm was formed.

The sensor prepared in this manner was sufficiently dried, immersed in a 1 mM/l potassium chloride aqueous solution for 2 hours, and tested.

TEST EXAMPLES 63 AND 64

After an oxidation/reduction film was formed on a BPG base in a similar manner to that in Example 62, it was dipped in an dipping solution (solvent: 5 ml of tetrahydrofuran) having the composition shown in Table 12 so as to form a potassium ion carrier film. Immersion was performed 20 times, and the film was dried upon each immersion with hot air at 100° C. or lower.

TABLE 12

| | Dopping Solution Composition (mg) | | |
|---|---|---|---|
| Example | Carrier | Polymeric Substance | Plasticizer |
| 63 | BC 18.1* | PVC** 292.7 | SD*** 659.9 |
| 64 | BC 19.0* | PVC** 299.4 | NO**** 664.5 |

*Bis[(benzo-15-crown-5)-4'-methyl] pimelate available from Dojindo Laboratories
**Polyvinyl chloride (polymerization degree: 1,050)
***Dioctyl Sebacate
****o-nitrophenyloctyl ether available from Dojindo Laboratories

TEST EXAMPLES 40–42

Figure 20:
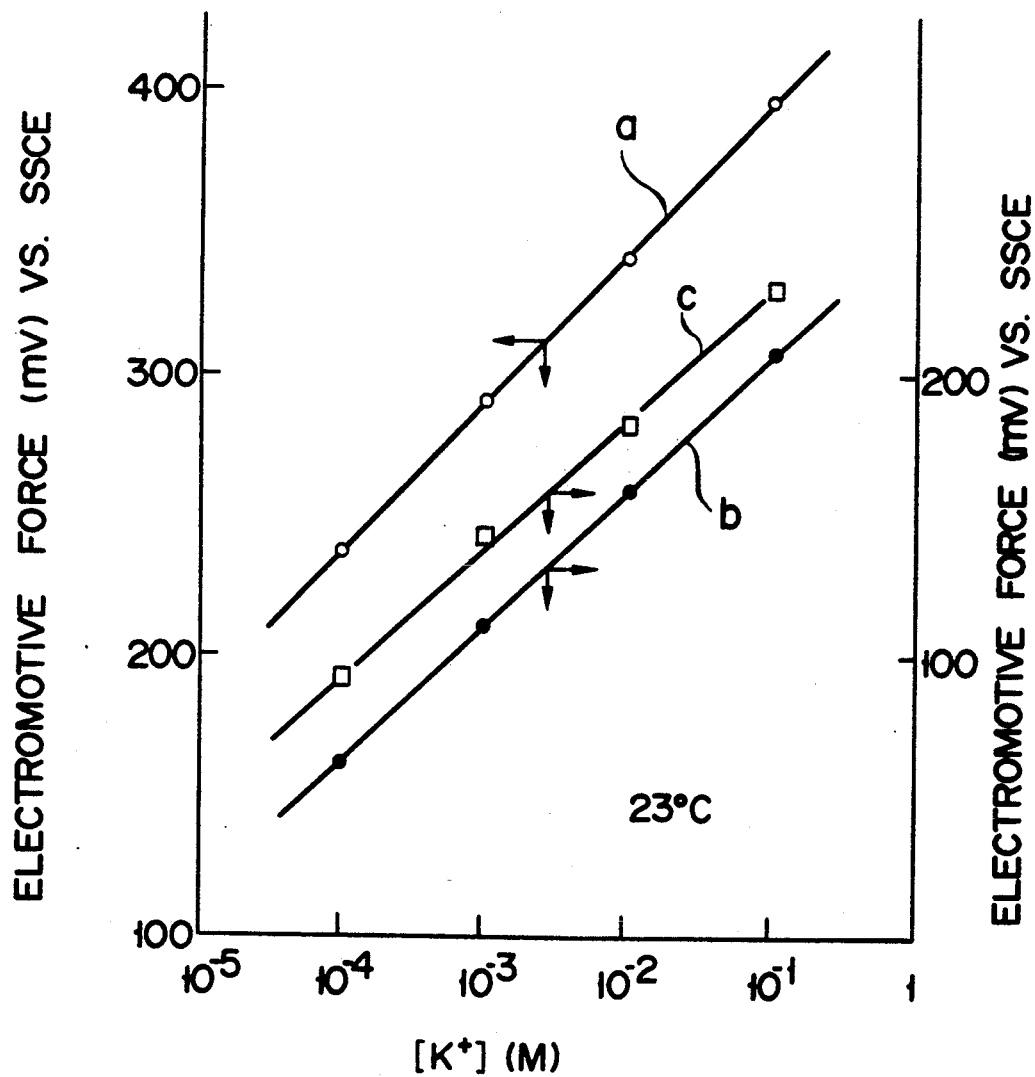

In order to measure the response of the sensors prepared in Examples 62 to 64 to potassium ions, the sensors were dipped together with SSCEs in a potassium aqueous solution containing $10^{-4}$ to $10^{-1}$ M/l of potassium ions. The electromotive forces of the respective sensors were measured (23° C.). FIG. 20 shows the relationship between the electromotive force (with reference to the SSCE) and the logarithmic value of the potassium ion concentration. Referring to FIG. 20, line a corresponds to the sensor of Example 62, line b corresponds to the sensor of Example 63, and line c corresponds to the sensor of Example 64. As can be seen from these results, the electromotive forces of these sensors have good linear relation with the logarithmic values of the potassium ion concentration and satisfy the Nernst equation. The time required for each sensor to reach a potential 95% of the equilibrium potential (95% response time) was also measured for each sensor, and the obtained results are shown in Table 13.

TABLE 13

| Sensor (Example No.) | Slope of Line -(mV/pH) | Linear K Ion Concentration Range | 95% Response Time |
|---|---|---|---|
| 62 | 53.1 | $10^{-4}$ to $10^{-1}$ | 30 sec or less |
| 63 | 48.1 | $10^{-4}$ to $10^{-1}$ | 1 min or less |
| 64 | 46.2 | $10^{-4}$ to $10^{-1}$ | 1 min or less |

In order to examine the influence of dissolved oxygen on the electromotive force of each potassium ion sensor, a difference between the electromotive force obtained when pure nitrogen gas (flow rate: 100 ml/min) was blown into the solution for 3 hours and that obtained when oxygen gas (flow rate: 100 ml/min) was blown into the solution for 5 hours was measured. As a result, for each sensor, the difference was within ±2 mV. This reveals that the potassium ion sensor of the present invention can measure the potassium ion concentration in a measuring solution without being adversely affected by the dissolved oxygen therein.

EXAMPLE 65

A sodium ion sensor having the structure as shown in FIG. 2 was prepared by the following method:

(i) A column having a diameter of 5 mm was cut from a plate of basal plane pyrolytic graphite (BPG: available from Union Carbide Corp.) A leading wire was connected to the bottom of the column with a conductive adhesive ("C-850-6" available from Amicon K.K.) The structure was covered with a heat shrinkable tube (available from Alpha Wire Inc.) such that the top face of the BPG projected slightly from the tube. The projecting end face of the BPG base was cleaved with a knife blade so as to expose a new surface. Electrooxidation polymerization was performed using the structure as a working electrode, a saturated sodium chloride calomel electrode (SSCE) as a reference electrode, and a platinum net as a counter electrode under the following conditions.

Electrolytic Solution

Acetonitrile containing 0.2M of sodium perchlorate as a supporting electrolyte and 0.5M of 2,6-xylenol as a reactive substance Electrolysis Conditions After the electrolysis potential was swept three times from 0 V to 1.5 V vs. SSEC (sweep rate: 50 mV/sec), constant potential electrolysis was performed at 1.5 V for 10 minutes.

In this manner, an electrooxidation polymer film of 2,6-xylenol (having a thickness of about 30 μm) was formed on the exposed surface of the BPG base. The polymer film was dark blue in color.

(ii) After the electrooxidation polymer coated electrode prepared in item (i) above was rinsed with water and dried, it was dipped in a sodium ion carrier substance containing a solution having the following composition and dried to form a sodium ion carrier film on the electrooxidation polymer film. Note that the dipping/drying process was repeated 30 times, and a sodium ion carrier film having a thickness of about 0.3 mm was formed.

Immersion Solution Composition

| | |
|---|---|
| Bis[(12-crown-4)methyl]methyl dodecylmalonate | 20.7 mg |
| Potassium tetrakis(p-chlorophenyl)borate | 4.5 mg |
| Polyvinyl chloride (polymerization degree: 1,050) | 270.3 mg |
| Di(2-ethylhexyl)sebacate | 536.9 mg |
| Tetrahydrofuran | 10 ml |

The sensor obtained in this manner was dried well, dipped in a 1 mM sodium chloride aqueous solution for 2 hours, and tested.

Test Example 43

The response of the sodium ion sensor prepared in Example 65 to sodium ions was examined by dipping it in a $8 \times 10^{-4}$ to $3 \times 10^{-1}$M sodium chloride aqueous solution together with an SSCE and measuring the electromotive force of the sensor. Measurement was performed at 37° C. The obtained results are shown in FIG. 21.

As can be seen from FIG. 21, the electromotive force had a good linear relation with the sodium ion concentration within a concentration range of $10^{-4}$ to $10^0$M. In the measurement of electromotive force at each concentration, time required for the sensor to reach a potential 95% of the equilibrium potential (95% response time) was within 1 minute.

Test Example 44

In order to examine the influence of dissolved oxygen on the electromotive force of the sodium ion sensor prepared in Example 65, the working electrode of Example 65 and a reference electrode (SSCE) were dipped in the same solution so as to saturate the film with the dissolved gas. A difference between the electromotive force when pure nitrogen gas (flow rate: 100 ml/min) was blown into the solution for 3 hours and that when oxygen gas (flow rate: 100 ml/min) was blown into the solution for 5 hours was measured. As a result, the difference in electromotive force was within ±2 mV. It is seen from this fact that the sensor of the present invention can measure the sodium ion concentration without being influenced by the dissolved oxygen in the measuring solution.

EXAMPLE 66

A disk (thickness: 5 mm; diameter: 5.0 mm) was cut from a plate of basal plane pyrolytic graphite (BPG). A lead wire (teflon coated copper wire) was connected to one end face of the disk with a conductive adhesive ("C-850-6" available from Amicon K.K.) The base was inserted into a heat shrinkable tube such that the end face of the base, not having the lead wire connected, slightly projected from the tube end face. The tube was allowed to shrink by heating so as to insulate the base. The projecting end face of the base was peeled by a thin layer so as to expose a new surface.

Electrooxidation polymerization was performed in a three electrode electrolysis cell under the following conditions using the base structure as a working electrode, a saturated sodium chloride calomel electrode (SSCE) as a reference electrode and a platinum net as a counter electrode. An electrooxidation polymer film was thus formed on the exposed surface of the base.

The electrolytic solution used was obtained by adding 10 mM/l of 1-aminopyrene and 10 mM/l of pyridine to an acetonitrile solvent containing 0.2 m/l of sodium perchlorate as a supporting electrolyte. Constant potential electrolysis was performed at +1.0 V (with reference to the SSCE) after the potential of the working electrode was swept at +1.0 V (with reference to the SSCE) from 0 V to +1.0 V at a sweeping speed of 50 mV/sec three times. Thus, an electrooxidation polymer film of 1-aminopyrene (redox polymer) was formed on the exposed surface of the base. The resultant redox polymer film has a thickness of about 30 μm. After the film was dried, a calcium ion carrier film was formed by the following method.

A solution was prepared by dissolving in 5 ml of tetrahydrofuran, 22.5 mg of calcium bis[(n-octylphenyl) phosphate], 8.6 mg of potassium tetrakis-p-chlorophenyl borate, 493.8 mg of dioctyl sebacate, and 251.1 mg of vinyl chloride (average polymerization degree: 1,050). The oxidation/reduction film was dipped in the resultant solution and dried, and the process was repeated to form a calcium ion carrier film having a thickness of about 0.3 mm.

TEST EXAMPLE 45

In order to examine the response of the calcium ion sensor prepared in Example 66 to calcium ion concentration, the sensor was dipped together with an SSCE in an aqueous solution containing $10^{-3}$ to $10^{-1}$ M/l of calcium chloride. The electromotive force of the sensor (with reference to the SSCE) was measured with an electrometer ("TR8652" available from Takeda Riken K. K.) (measurement temperature: 25° C.±0.1° C.). As a result, the electromotive force and the calcium ion concentration had a linear relation as shown in FIG. 22. The line has a slope of about 19 mV/log{[Ca$^{2+}$](M)}.

EXAMPLE 67

After a BPG base was prepared following the same procedures as in Example 66, an electrooxidation polymer film of 2,6-dimethylphenol was formed using the following electrolytic solution and electrolysis conditions.

Electrolytic Solution

Acetonitrile containing 0.2M of sodium perchlorate and 0.5M of 2,6-dimethylphenol Electrolysis Conditions After the base potential was swept within a range of 0 V to 1.5 V (with reference to the SSCE) three times (sweep rate: 50 mV/sec), constant potential electrolysis at 1 V (with reference to the SSCE) was performed for 10 minutes.

A calcium ion carrier film having a thickness of about 0.4 mm similar to that in Example 66 was deposited on the resultant redox polymer film. The objective calcium ion sensor was thus prepared.

TEST EXAMPLE 46

Figure 23:
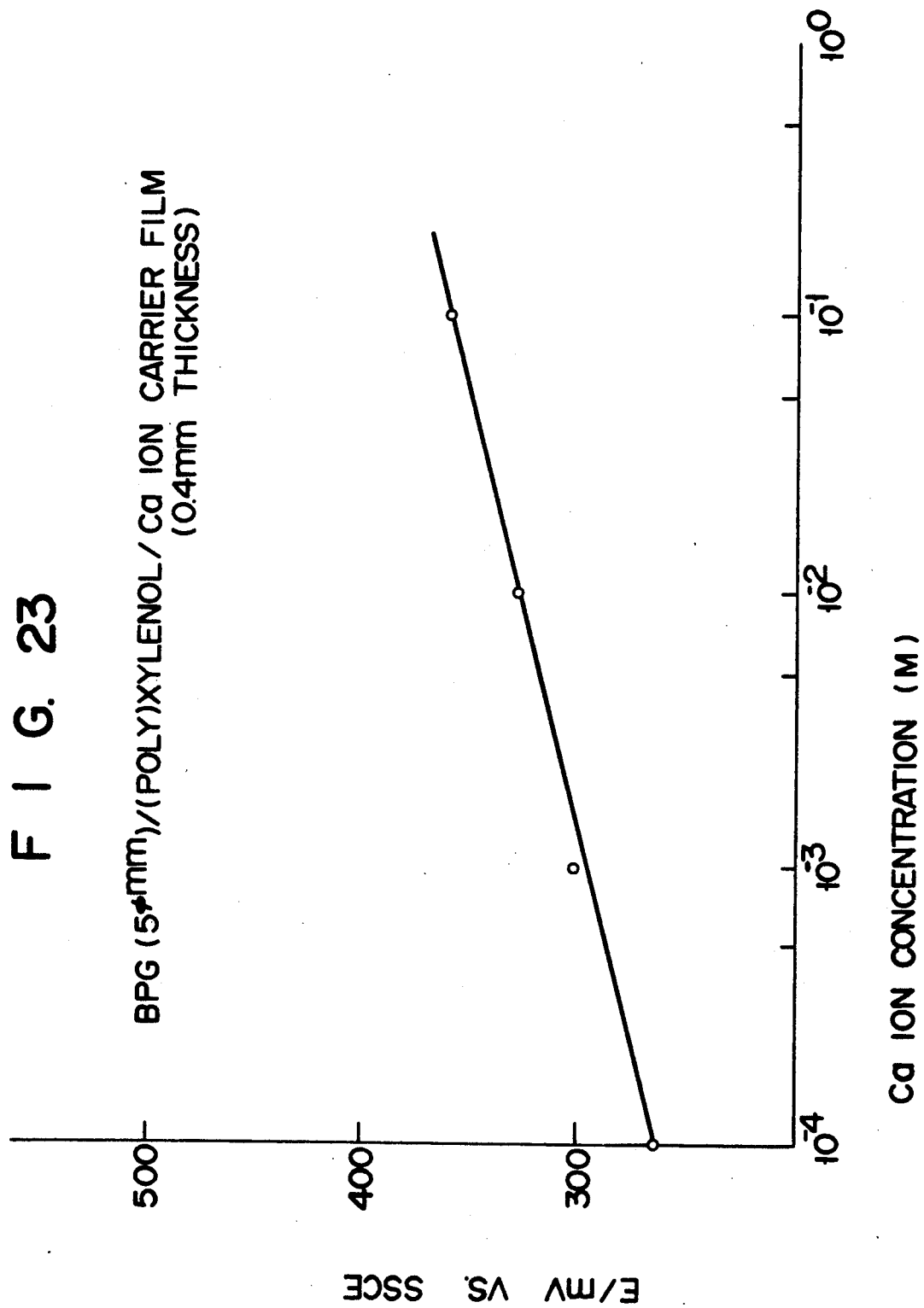

When the characteristics of the calcium ion sensor prepared in Example 67 were examined following the same procedures as in Example 45, the electromotive force of the ion sensor and the calcium ion concentration had a linear relation as shown in FIG. 23. The 95% response time was 1 to 2 minutes.

TEST EXAMPLE 47

Figure 24:
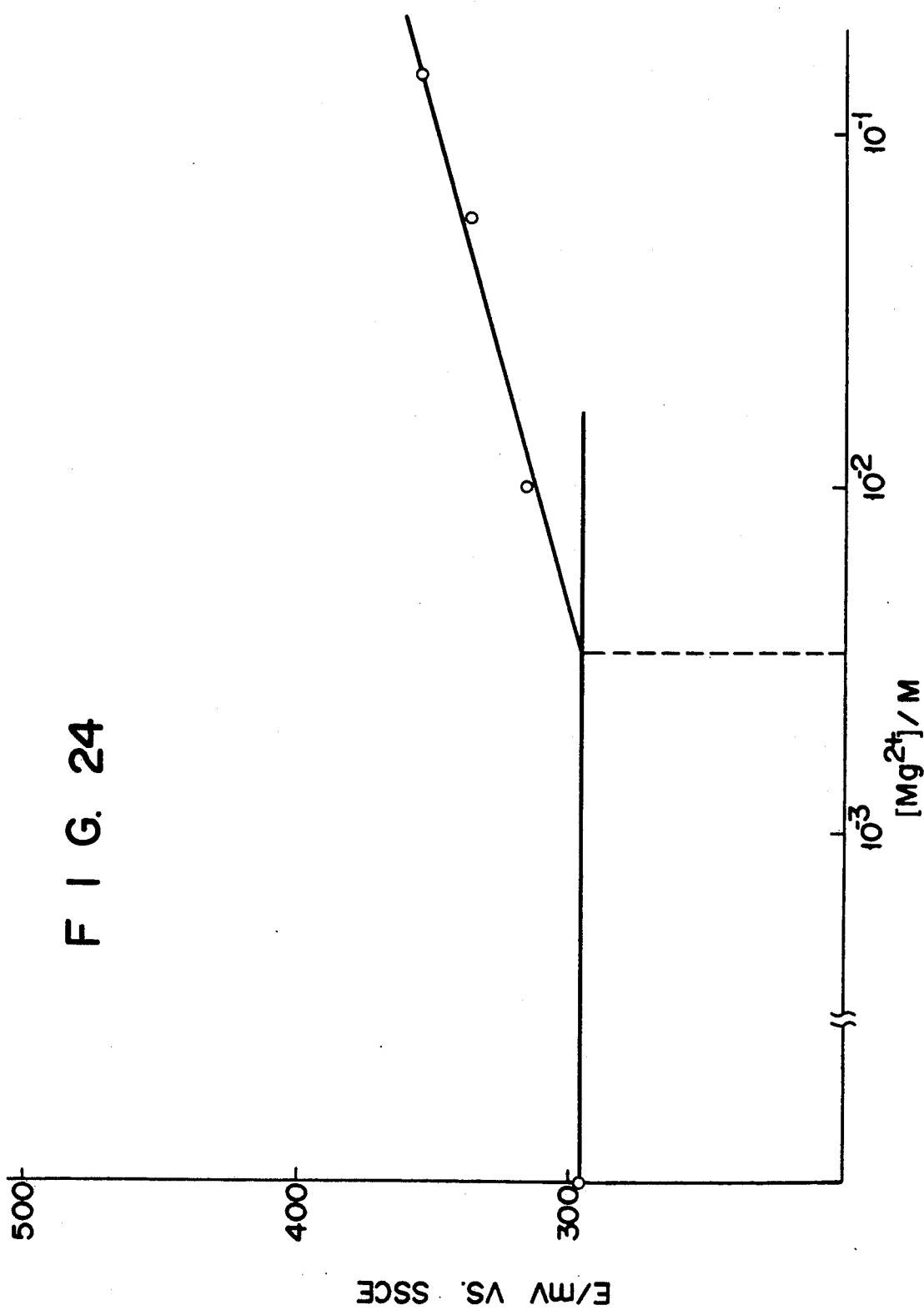

Using the calcium ion sensor of Example 67, the magnesium ion selection coefficient was measured in the presence of magnesium ions (25° C.±0.1° C.), and $logK_{Ca}{}^{Pot}Mg$ was $-3.33$. This value is significantly smaller than the value, $-1.9$ to $-2.0$ of the conventional calcium ion sensor. It is thus demonstrated that the calcium ion sensor of the present invention is less prone to the influence of Mg ions (FIG. 24).

TEST EXAMPLE 48

The calcium ion selection coefficient in the presence of sodium ions was measured (25° C.±0.1° C.) using the calcium ion sensor of Example 67. The $logK_{Ca}{}^{Pot}Na$ was $7.5 \times 10^{-4}$. This reveals that the calcium ion sensor of the present invention is less prone to the influence of sodium ions.

EXAMPLE 68

After an electrooxidation polymer film of 2,6-dimethylphenol was formed on the surface of a BPG base following the same procedures as in Example 66, a solution of the following composition was coated and dried to form a calcium ion carrier film.

| Immersion Solution Composition | |
| --- | --- |
| Calcium bis[di(n-octyl) phosphate] | 80 mg |
| DOS (plasticizer) | 360 mg |
| Di-n-octyl phosphate (plasticizer) | 360 mg |
| Polyvinyl chloride | 340 mg |
| THF | 10 ml |

When the magnesium ion selection coefficient of the obtained calcium ion sensor was measured, the calcium ion concentration could be measured without the influence of the magnesium ions within the range of the $[Mg^{2+}]$ between $10^{-1}M$ and $10^{-2}M$.

EXAMPLE 69

(i) A column having a diameter of 5 mm was cut from a plate of basal plane pyrolytic graphite (BPG: available from Union Carbide Corp.) A leading wire was connected to the bottom of the column with a conductive adhesive ("C-850-6" available from Amicon K.K.) The structure was covered with a heat shrinkable tube such that a top surface 21a of the BPG projected slightly. The projecting end of the BPG base was peeled with a knife blade to expose a new surface. Electrooxidation polymerization was performed under the following conditions using the structure as a working electrode, a saturated sodium chloride calomel electrode (SSCE) as a reference electrode and a platinum net as a counter electrode.

Electrolytic Solution

Acetonitrile containing 0.2M of sodium perchlorate as a supporting electrolyte and 0.5M of 2,6-xylenol as a reactive substance

Electrolysis Conditions

After sweeping the electrolysis potential three times from 0 V to 1.5 V (sweeping speed: 50 mV/sec), constant potential electrolysis at 1.5 V was performed for 10 minutes.

After the polymer film was rinsed with a methanol solution to remove nonreacted 2,6-xylenol, it was rinsed with water, dipped in 0.1M sodium chloride solution for 1 hour, rinsed with water and dried.

(ii) The polymer film prepared in item (i) was dipped in a chlorine ion carrier substance containing solution of the following composition and was dried to form a chlorine ion carrier film 14 on the polymer film. The dipping and drying process was repeated 20 times, and a chlorine ion carrier film having a thickness of about 0.3 mm was formed.

| Immersion Solution Composition | |
| --- | --- |
| Tetraphenyltinchloride | 62.7 mg |
| Polyvinyl chloride (avarage polymerization degree: 1,050) | 324.7 mg |
| Dioctyl sebacate | 725.3 mg |
| Tetrahydrofuran | 10 ml |

After the sensor was dried well, it was dipped in a 1 mM sodium chloride aqueous solution for 2 hours, and tested.

TEST EXAMPLE 48

The response of the chlorine ion sensor prepared in Example 67 was examined by measuring the electromotive force of the sensor by dipping the sensor in a $10^{-4}$ to $10^0 M$ sodium chloride solution. Measurement was performed at 37° C. The obtained results are shown in FIG. 25.

Figure 25:
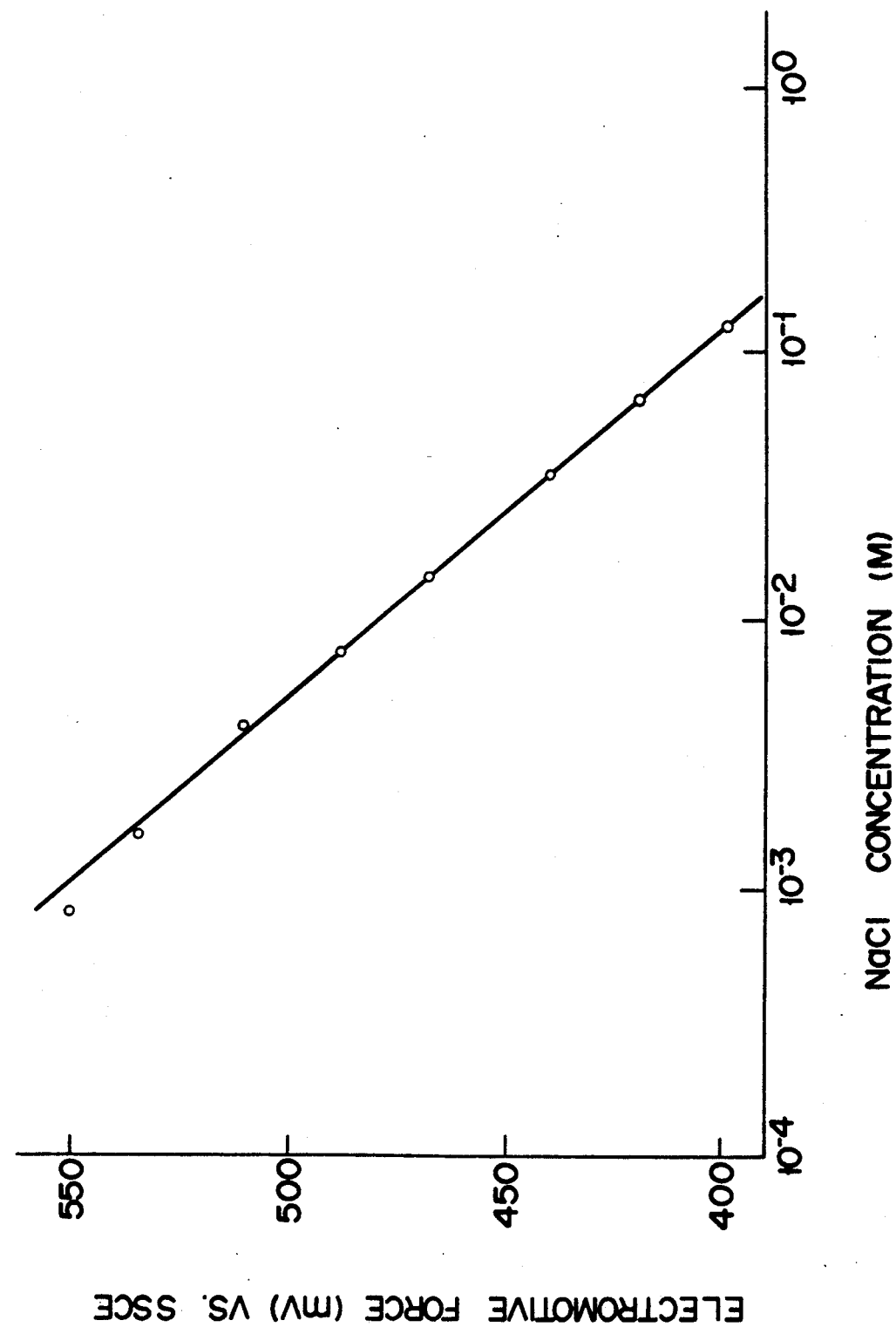

As can be seen from FIG. 25, the electromotive force and the chlorine ion concentration had a linear relation within a concentration range of $10^{-4}$ to $10^0 M$. The time required for the sensor to reach a potential 95% of the equilibrium potential (95% response time) was within 1 minute.

TEST EXAMPLE 50

In order to examine the influence of dissolved oxygen on the electromotive force of the chlorine ion sensor prepared in Example 69, the oxygen partial pressure $pO_2$ of the measuring solution of Test Example 48 was changed within the range of 0 to 700 mmHg and the electromotive force was measured as in Test Example 48. The difference in electromotive force was within $\pm 2$ mV. It was thus demonstrated that the chlorine ion sensor of the present invention can measure the chlorine ion concentration without being influenced by the dissolved oxygen in the measuring solution.

EXAMPLES 70-78

As in Example 1, BPG disks were prepared and an electrooxidation was performed under the conditions below to form an electrooxidation polymer film on each BPG disk.

Electrolytic solution

| Supporting electrolyte | 0.2M NaClO$_4$ |
| Monomer | 0.5M 2, 6-xylenol |
| Solvent | Acetonitorile |

Electrolytic condition

After sweeping the potential of the working electrode at a speed of 50 mV/sec within a range of 0 V to +1.5 V (with reference to the SSCE) three times, constant potential electrolysis was performed at +1.5 V (with reference to the SSCE) for 10 minutes.

The BPG disks coated with the polymer film of 2, 6-xylenol were washed with water and dried. Then, the disks were repeatedly immersed in a tetrahydrofuran solution indicated in Table 14 below and dried to form a hydrogencarbonate ion carrier on the polymer film. Thus, desired 9 hydrogencarbonate ion sensors were prepared.

TABLE 14

| Example | Carrier Substance | | Plasticiser | | Polyvinyl Chloride | Immersion Time | Thickness of Ion carrier Film |
|---|---|---|---|---|---|---|---|
| 70 | TDA-Cl | 17.9 mg | NPOE | 435.0 mg | 221.8 mg | 15 | 0.3 mm |
| 71 | TDA-Cl | 14.0 | DOS | 664.2 | 221.9 | 15 | 0.3 |
| 72 | TDA-Cl | 17.6 | DOS | 310.6 | 154.5 | 15 | 0.4 |
| 73 | TDDA-Cl | 13.3 | NPOE | 362.2 | 188.9 | 15 | 0.3 |
| 74 | TDDA-Cl | 19.1 | DOA | 371.4 | 185.9 | 15 | 0.3 |
| 75 | TDDA-Cl | 12.0 | DOS | 351.8 | 180.7 | 15 | 0.4 |
| 76 | TDDA-OH | 11.0 | NPOE | 344.1 | 176.8 | 15 | 0.4 |
| 77 | TDDA-OH | 13.6 | DOA | 441.2 | 210.4 | 15 | 0.4 |
| 78 | TDDA-OH | 13.0 | DOS | 382.5 | 186.8 | 15 | 0.4 |

Note:
TDA-Cl: Tri-n-decylammonium chloride
TDDA-Cl: Tri-n-dodecylammonium choride
TDDA-OH: Tri-n-dodecylammonium hydroxide
NPOE: O-nitrophenyl octyl ether
DOA: Di(2-ethylhexyl) adipate
DOS: Di(2-ethylhexyl) sebacate

TEST EXAMPLES 51

The sensor of Example 72 was dipped in a $10^{-3}$ to $10^{-1}$M solution of sodium hydrogencarbonate together with SSCE, and the electromotive force of the sensor was determined against the concentration of the hydrogencarbonate ions. The results are shown in FIG. 28.

Figure 28:
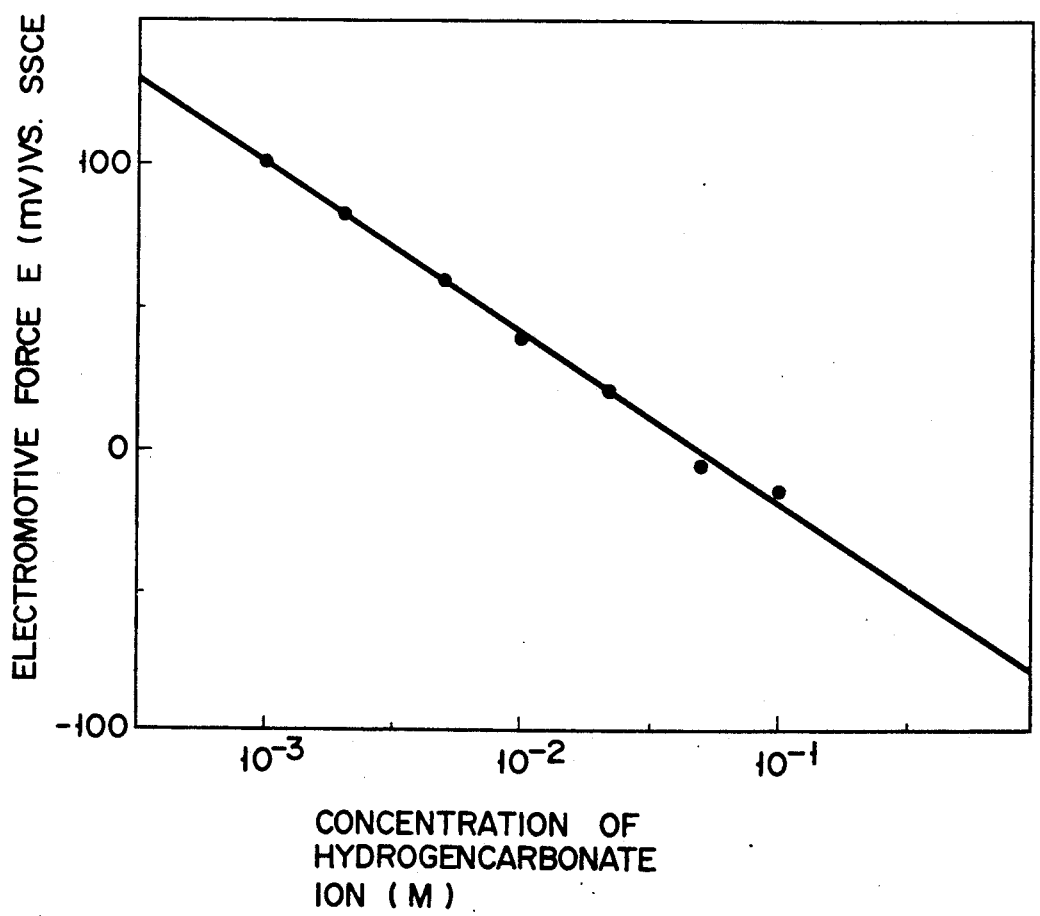
FIG. 28 is a graph showing the characteristics of an ion sensor according to the present invention.

As seen from FIG. 28, a good linear relationship is obtained between the electromotive force and the concentration of hydrogencarbonate ions within a concentration of $10^{-3}$ to $10^{-1}$M.

The sensors of Examples 70, 71 and 73 to 78 were similarly tested, and good linear relations were obtained. The slope of the obtained lines are shown in Table 15 below. Further, it was found that 95% response time was 1 minute or less, and the electromotive force was not affected by dissolved oxygen partial pressure change from 700 to 0 mmHg within a tolerance of ±2 mV.

TABLE 15

| | s mV/log[HCO$_3^-$] | |
|---|---|---|
| Example 70 | −38.4 | −2.79 |
| 71 | −61.0 | — |
| 72 | −60.2 | −2.78 |
| 73 | −39.4 | −2.68 |
| 74 | −60.7 | −2.73 |
| 75 | −63.4 | −2.70 |
| 76 | −45.4 | −2.72 |
| 77 | −64.4 | −2.68 |
| 78 | −69.6 | −2.55 |

Note: E = E

TEST EXAMPLE 52

In order to determine hydrogencarbonate ion selectivity of the sensors of Examples 70 to 78, the electromotive force of the sensors was determined as in Test Example 51, except that the aqueous sodium hydrogencarbonate solution further contained 0.15M of sodium chloride. Selectivity coefficient $K_{HCO_3}^{Pot}._{Cl^-}$ was determined. The results are indicated in Table 15 above.

As described above, the ion sensor of the present invention generates a potential corresponding to a concentration of a specific type of ions in an aqueous solution by using a carrier substance in the ion carrier film as a carrier of the specific type of ions whose concentration is to be measured. The sensor has a quick response and is substantially not prone to the influence of other substances which may be present in the solution (e.g., dissolved oxygen, and ions of types other than the specific type of ions). Therefore, the ion sensor of the present invention can measure the concentration of a specific type of ions in an aqueous solution quickly and with precision. Unlike a conventional ion sensor, the sensor of the present invention does not require a standard internal solution chamber and can be rendered compact in size. The sensor has excellent stability over time and allows stable ion concentration measurement over a long period of time with good reproducibility.

What is claimed is:

1. An ion sensor wherein a specific type of ion in an aqueous solution is measured by potential response, comprising:
   a conductor base;
   a reversible redox polymer film formed directly on a surface of said conductor base; and
   an ion carrier film formed directly on a surface of said redox polymer film and containing an ion carrier substance for allowing the specific type of ions to permeate from the aqueous solution to said polymer film;

wherein said conductor base is made of a conductive carbon compound; and wherein said redox polymer film is capable of performing a reversible oxidation/reduction reaction of quinone-hydroquinone, and is formed by electrooxidation polymerization of at least one first compound selected from the group consisting of phenol, 3,5-, 2,6- and 3,4-xylenols, 2-hydroxy pyridine, o- and m-benzyl alcohols, o-, m- and p-hydroxybenzaldehydes, o-, m- and p-hydroxyacetophenones, o-, m- and p-hydroxypropiophenones, o-, o-, m- and p-benzophenols, o-, m- and p-hydroxybenzophenones, o-, m- and p-carboxyphenols, diphenylphenol, 2-methyl-8-hydroxyquinoline, 5-hydroxy-1,4-naphthoquinone, 4-(p-hydroxyphenyl)-2-butanone, 1,5-dihydroxy-1,2,3,4-tetrahydronaphthalene, bisphenol A, salicylanilide, 5- and 8-hydroxyquinolines, 1,8-dihydroxyanthraquinones, 1,2,5,8-tetrahydroxyquinalizarin, 1-amino-4-hydroxyanthraquinone, 1-aminoanthraquinone, purpurin, and anthrarufin.

2. An ion sensor according to claim 1, wherein said redox polymer film contains at least one electrolyte selected from the group consisting of, dipotassiumhydrogenphosphate, sodium perchlorate, sulfuric acid, sulfates, tetrafluoroborate, tetraphenylborate, phosphates and phosphoric acid.

3. An ion sensor according to claim 1, wherein said ion carrier substance is a hydrogen ion carrier substance.

4. An ion sensor according to claim 3, wherein said hydrogen ion carrier substance is at least one member selected from the group consisting of amines represented by:

(wherein each of $R^1$, $R^2$ and $R^3$ is an alkyl group, at least two of which are alkyl groups having 8 to 18 carbon atoms), and pyridine derivatives represented by:

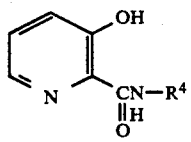

(wherein $R^4$ is an alkyl group having 8 to 18 carbon atoms).

5. An ion sensor according to claim 1, wherein said ion carrier substance is a potassium ion carrier substance.

6. An ion sensor according to claim 5, wherein said potassium ion carrier substance is at least one member selected from the group consisting of valinomycin, bis(15-crown-5), nonactin, monactin, and crown ether compounds.

7. An ion sensor according to claim 1, wherein said ion carrier substance is a sodium ion carrier substance.

8. An ion sensor according to claim 7, wherein said sodium ion carrier substance is at least one member selected from the group consisting of bis[(12-crown-4)-methyl]dodecylamalonate, N,N,N,N-tetrapropyl-3,6-dioxanate-diamide, 3-methoxy-N,N,N,N-tetrapropyl-1,2-phenylenedioxydiacetoamide, (−)-(R,R)-4,5-dimethyl-N,N,N,N-tetrapropyl-3,6-dioxaoctanediamide, 4-methyl-N,N,N,N-tetrapropyl-3,6-dioxaoctanediamide, N,N,N,N-tetrapropyl-1,2-phenylenedioxydiacetoamide, N,N,N,N-tetrapropyl-2,3-naphtharenedioxydiacetoamide, 4-t-butyl-N,N,N,N-tetrapropyl-1,2-cyclohexanedioxydiaceto amide, 4-t-butyl-N,N'-di[(11-ethoxycarbonyl)undecyl]-N,N'-dimethyl-1,2-cyclohexanedioxydiacetoamide, cis-N,N,N,N-tetrapropyl-1,2-cyclohexanedioxydiacetoamide, and trans-N,N,N,N-tetrapropyl-1,2-cyclohexanedioxydiacetoamide.

9. An ion sensor according to claim 1, wherein said ion carrier substance is a calcium ion carrier substance.

10. An ion sensor according to claim 9, wherein said calcium ion carrier substance is at least one member selected from the group consisting of calcium-bis-[di-(n-octylphenyl)phosphate], (−)-(R,R)-N,N'-bis[(11-ethoxycarbonyl)undecyl]-N,N'-4,5-tetramethyl-3,6-dioxaoctanediamide, and calcium bis[di(n-decyl) phosphate].

11. An ion sensor according to claim 1, wherein said ion carrier substance is a chlorine ion carrier substance.

12. An ion sensor according to claim 11, wherein said chlorine ion carrier substance is at least one member selected from the group consisting of quaternary ammonium salts represented by the general formula:

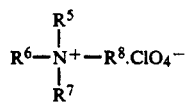

(wherein each of $R^5$, $R^6$, $R^7$ and $R^8$ is independently an alkyl group having 6 to 18 carbon atoms, and at least one of $R^5$ to $R^8$ can contain a hydrogen atom or a methyl group), and triphenyl tin chloride.

13. An ion sensor according to claim 1, wherein said ion carrier substance contains at least one electrolyte selected from the group consisting of sodium tetrakis(p-chlorophenyl)borate, and potassiumtetrakis (p-chlorophenyl)borate; and compounds represented by general formulas:

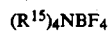

and

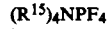

(wherein each $R^{15}$ is independently an alkyl group).

14. An ion sensor according to claim 1, wherein said ion carrier film comprises a polymeric substance selected from the group consisting of polyvinyl chloride, a vinyl chloride-ethylene copolymer, polyester, polyacrylamide, cellulose-based substances, polyurethane, and silicone resin.

15. An ion sensor according to claim 14, wherein said polymeric substance is polyvinyl chloride in a paste form.

16. An ion sensor according to claim 1, wherein said redox polymer film has a thickness of 0.1 μm to 0.2 mm.

17. An ion sensor according to claim 1, wherein said ion carrier film has a thickness of 50 μm to 10 mm.

18. An ion sensor according to claim 1, wherein said ion carrier substance is selected from the group consisting of a quaternary ammonium salt of the formula:

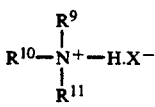

where $R^9$ to $R^{11}$ are independently alkal groups having 8 to 18 carbon atoms and $X^-$ is $Cl^-$, $Br^-$ or $OH^-$; a tertiary amine of the formula

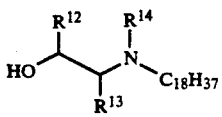

where $R^{12}$ is phenyl group, methyl group or hydrogen atom, $R^{13}$ is hydrogen atom or methyl group, and $R^{14}$ is hydrogen atom, methyl group or octadecyl group; and the compounds of formulas:

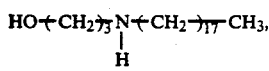

and

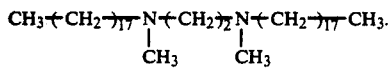

19. An ion sensor according to claim 1, wherein said ion carrier film has a thickness of 300 μm to 1 mm.

20. An ion sensor wherein a specific type of ion in an aqueous solution is measured by potential response, comprising:
 a conductor base;
 a reversible redox polymer film formed directly on a surface of said conductor base; and
 an ion carrier film formed directly on a surface of said redox polymer film and containing an ion carrier substance for allowing the specific type of ions to permeate from the aqueous solution to said polymer film;
 wherein said conductor base is made of a conductive carbon compound; and
 wherein said redox polymer film is capable of performing a reversible oxidation/reduction reaction of amine-quinoid, and formed by electrooxidation polymerization of at least one first compound selected from the group consisting of aniline, 1-aminopyrene, 1,2-, 1,6- and 1,8-diaminopyrenes, 1-9, 10-diaminophenanthrenes, 1-aminoanthraquinone, p-phenoxyaniline, o-phenylenediamine, p-chloroaniline, 3,5-dichloroaniline, 2,4,6-trichloroaniline, N-phenyl-p-phenylenediamine, and N-methylaniline.

21. An ion sensor according to claim 20, wherein said redox polymer film further comprises at least one electrolyte selected from the group consisting of, dipotassium-hydrogenphosphate, sodium perchlorate, sulfuric acid, sulfates, tetrafluoroborate, tetraphenylborate, phosphates and phosphoric acid.

22. An ion sensor according to claim 20, wherein said ion carrier substance is a hydrogen ion carrier substance.

23. An ion sensor according to claim 20, wherein said ion carrier substance is a potassium ion carrier substance.

24. An ion sensor according to claim 20, wherein said ion carrier substance is a sodium ion carrier substance.

25. An ion sensor according to claim 20, wherein said ion carrier substance is a calcium ion carrier substance.

26. An ion sensor according to claim 20, wherein said ion carrier substance is a chlorine ion carrier substance.

27. An ion sensor according to claim 20, wherein said ion carrier substance contains at least one electrolyte selected from the group consisting of sodium tetrakis(p-chlorophenyl) borate, and potassiumtetrakis (p-chlorophenyl)borate; and compounds represented by general formulas:

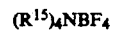

and

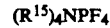

(wherein each $R^{15}$ is independently an alkyl group).

28. An ion sensor according to claim 20, wherein said ion carrier film comprises a polymeric substance selected from the group consisting of polyvinyl chloride, a vinyl chloride-ethylene copolymer, polyester, polyacrylamide, cellulose-based substances, polyurethane, and silicone resin.

29. An ion sensor according to claim 20, wherein said redox polymer film has a thickness of 0.1 μm to 0.2 mm.

30. An ion sensor according to claim 20, wherein said ion carrier film has a thickness of 50 μm to 10 mm.

31. An ion sensor according to claim 20, wherein said ion carrier substance is selected from the group consisting of a quaternary ammonium salt of the formula:

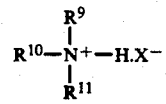

where $R^9$ to $R^{11}$ are independently alkyl groups having 8 to 18 carbon atoms and $X^-$ is $Cl^-$, $Br^-$ or $OH^-$; a tertiary amine of the formula

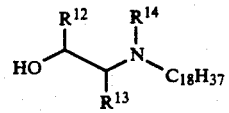

where $R^{12}$ is phenyl group, methyl group or hydrogen atom, $R^{13}$ is hydrogen atom or methyl group, and $R^{14}$ is hydrogen atom, methyl group or octadecyl group; and the compounds of formulas:

and

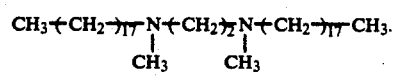

32. An ion sensor according to claim 20, wherein said ion carrier film has a thickness of 300 μm to 1 mm.

33. An ion sensor according to claim 1 or 20 wherein said conductor base is made of basal plane pyrolytic graphite or glassy carbon.

* * * * *